(12) United States Patent
Worrell

(10) Patent No.: US 11,364,052 B2
(45) Date of Patent: Jun. 21, 2022

(54) SCISSOR SLEEVE ASSEMBLY PROTECTION

(71) Applicant: Ethicon LLC, Guaynabo, PR (US)

(72) Inventor: Barry Christian Worrell, Maineville, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 657 days.

(21) Appl. No.: 16/280,597

(22) Filed: Feb. 20, 2019

(65) Prior Publication Data

US 2019/0314060 A1  Oct. 17, 2019

Related U.S. Application Data

(63) Continuation-in-part of application No. 15/955,226, filed on Apr. 17, 2018.

(51) Int. Cl.
*A61B 17/34* (2006.01)
*A61B 17/00* (2006.01)

(52) U.S. Cl.
CPC ...... *A61B 17/3496* (2013.01); *A61B 17/3417* (2013.01); *A61B 17/3476* (2013.01); *A61B 17/00234* (2013.01)

(58) Field of Classification Search
CPC ............ A61B 18/1442; A61B 18/1445; A61B 18/085; A61B 2018/1452; A61B 2018/00607; A61B 2018/0063; A61B 2018/0225; A61B 17/3496; A61B 17/3417; A61B 17/0024; A61B 17/3476; A61B 17/295; A61B 2017/00473; A61B 2017/00929; A61B 2017/00862; A61B 2017/2829; A61B 2090/0427; A61B 2090/0801; A61B 2090/08021; A61B 2090/0811; A61B 34/30
USPC ........................ 606/174, 205, 232, 41, 50–52
See application file for complete search history.

(56) References Cited

U.S. PATENT DOCUMENTS

| 7,824,401 B2 | 11/2010 | Manzo et al. |
| 7,897,035 B2 | 2/2011 | Garrison et al. |
| 8,241,283 B2 | 8/2012 | Guerra et al. |
| 8,361,072 B2 | 1/2013 | Dumbauld et al. |

(Continued)

FOREIGN PATENT DOCUMENTS

| EP | 1915957 A2 | 4/2008 |
| EP | 3064149 A2 | 9/2016 |

(Continued)

OTHER PUBLICATIONS

ISR/WO from PCT/IB2019/053134 (that claims priority to the parent of the present application) dated Aug. 5, 2019.

*Primary Examiner* — Thomas A Giuliani
(74) *Attorney, Agent, or Firm* — Vorys, Sater, Seymour and Pease LLP

(57) ABSTRACT

A sleeve insertion assembly includes a sleeve inserter defining an inner chamber and having a distal end and a proximal end opposite the distal end, a sleeve receivable within the inner chamber, and a blade guard receivable within the sleeve and having a cylindrical body that defines an interior and an open end. The open end is sized to receive jaw members of an end effector into the interior but prevent the end effector from entering the interior, and the blade guard is forced out of the sleeve when the sleeve is installed on the end effector.

19 Claims, 10 Drawing Sheets

(56) References Cited

U.S. PATENT DOCUMENTS

| | | | |
|---|---|---|---|
| 8,394,095 | B2 | 3/2013 | Garrison et al. |
| 8,696,667 | B2 | 4/2014 | Guerra et al. |
| 9,138,284 | B2 | 9/2015 | Krom et al. |
| 2004/0267254 | A1 | 12/2004 | Manzo et al. |
| 2006/0079884 | A1 | 4/2006 | Manzo |
| 2006/0079934 | A1 | 4/2006 | Ogawa |
| 2007/0073247 | A1 | 3/2007 | Ewaschuk |
| 2012/0010611 | A1* | 1/2012 | Krom .................... A61B 90/04 606/41 |
| 2014/0005474 | A1* | 1/2014 | Farin .................... A61B 1/3132 600/104 |
| 2015/0359587 | A1 | 12/2015 | Krom et al. |
| 2016/0213434 | A1 | 7/2016 | Lohmeier |

FOREIGN PATENT DOCUMENTS

| | | |
|---|---|---|
| GB | 2552855 B | 2/2018 |
| JP | 2005000352 A | 1/2005 |
| WO | 2013009156 A2 | 1/2013 |
| WO | 2015023865 A1 | 2/2015 |

* cited by examiner

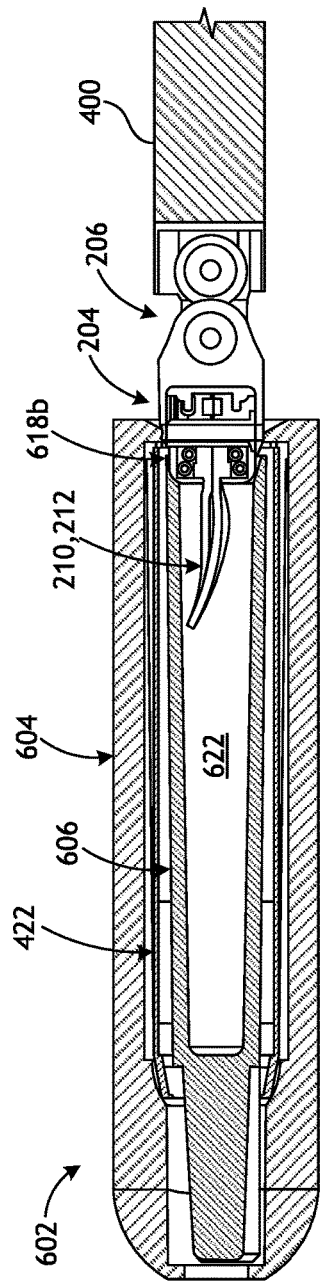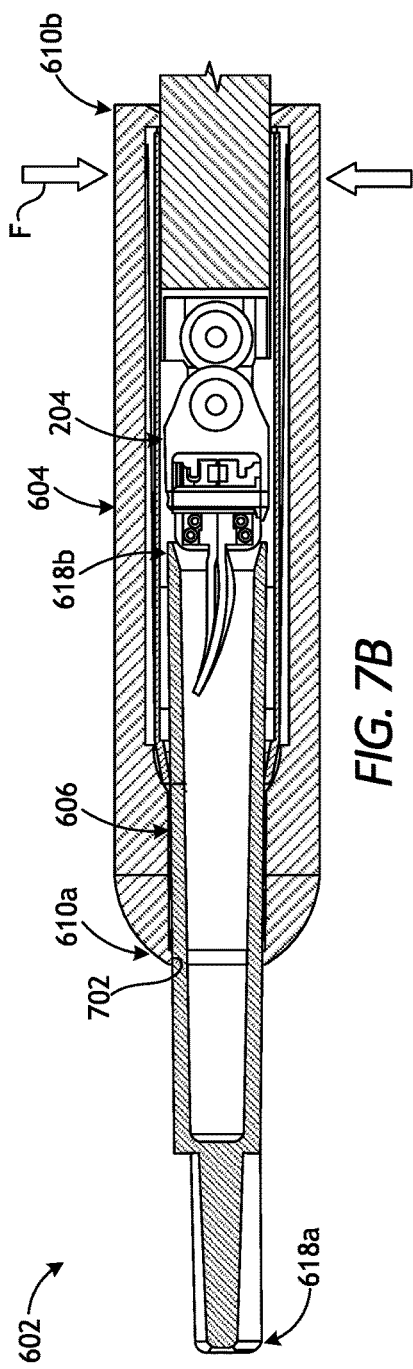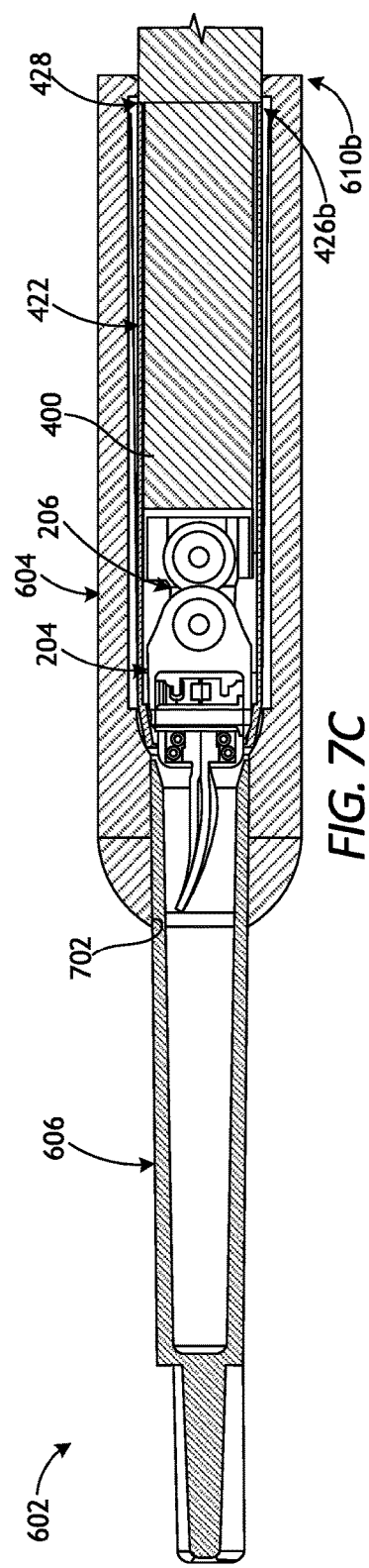

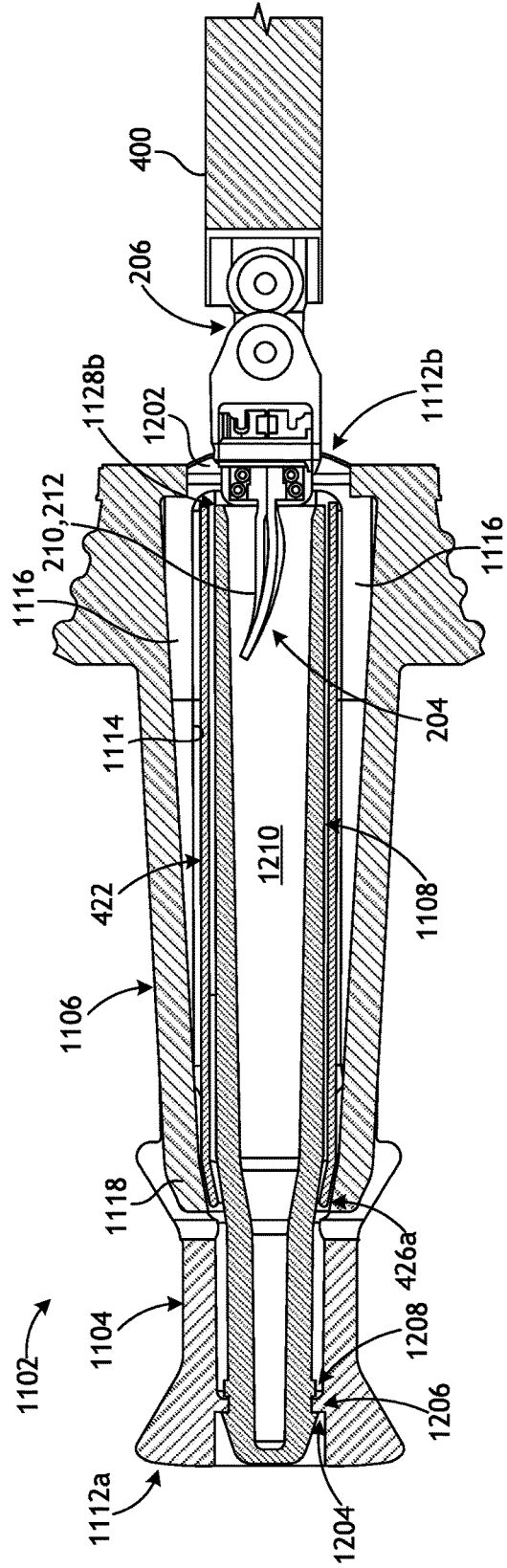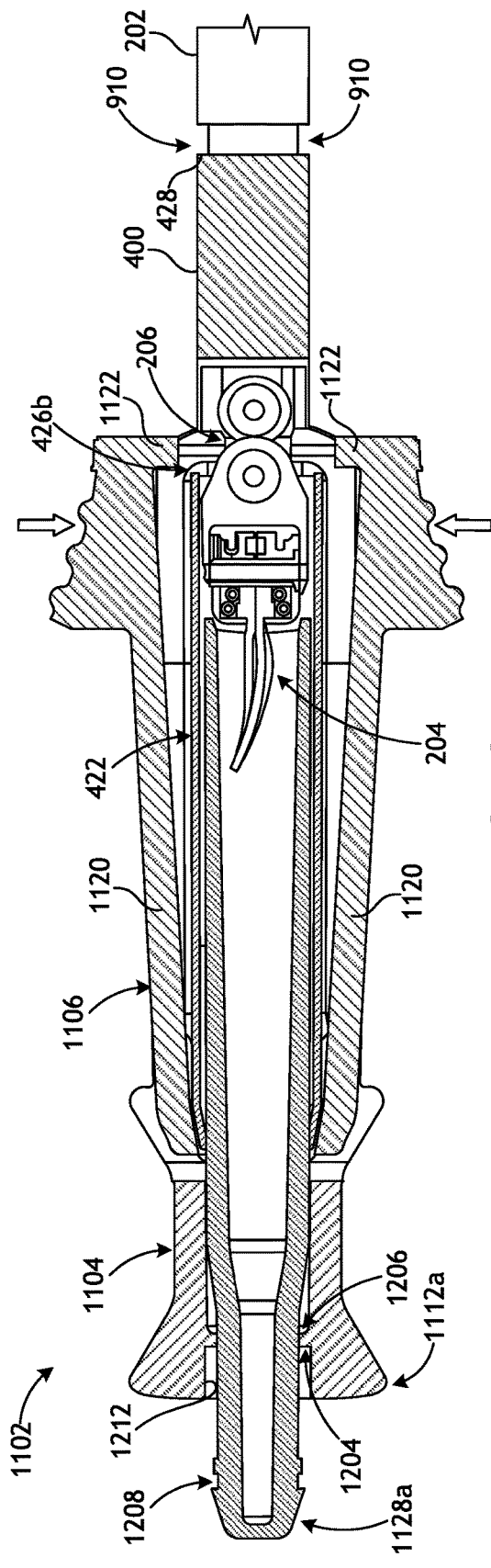
FIG. 12A
FIG. 12B

SCISSOR SLEEVE ASSEMBLY PROTECTION

CROSS-REFERENCE TO RELATED APPLICATIONS

The present application is a continuation-in-part of and claims priority to U.S. patent application Ser. No. 15/955,226, filed on Apr. 17, 2018, the contents of which are hereby incorporated by reference.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. Although not necessary, the instrument's end effector can be articulated (moved) using a cable driven motion system that incorporates one or more drive cables that extend through the wrist joint. A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

Some surgical tools, commonly referred to as electrosurgical instruments, are electrically energized. An electrosurgical instrument has a distally mounted end effector that includes one or more electrodes. When supplied with electrical energy, the end effector electrodes are able to generate heat sufficient to cut, cauterize, and/or seal tissue.

Electrosurgical instruments can be configured for bipolar or monopolar operation. In bipolar operation, current is introduced into and returned from the tissue by active and return electrodes, respectively, of the end effector. Electrical current in bipolar operation is not required to travel long distances through the patient before returning to the return electrode. Consequently, the amount of electrical current required is minimal, which greatly reduces the risk of accidental ablations and/or burns. In addition, the two electrodes are closely spaced and generally within the surgeon's field of view, which further reduces the risk of unintended ablations and burns.

In monopolar operation, current is introduced into the tissue by an active end effector electrode (alternately referred to as a "source electrode") and returned through a return electrode (e.g., a grounding pad) separately located on a patient's body. Monopolar electrosurgical instruments facilitate several surgical functions, such as cutting tissue, coagulating tissue to stop bleeding, or concurrently cutting and coagulating tissue. The surgeon can apply a current whenever the conductive portion of the instrument is in electrical proximity with the patient, permitting the surgeon to operate with monopolar electrosurgical instruments from many different angles.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 7A-7C are progressive cross-sectional side views of the sleeve insertion assembly of FIGS. 6A-6B showing example sleeve installation, according to one or more embodiments.

FIGS. 12A and 12B are progressive cross-sectional side views of the sleeve insertion assembly of FIGS. 11A-11B showing example sleeve installation, according to one or more embodiments.

DETAILED DESCRIPTION

The present disclosure is related to robotic surgical systems that incorporate electrosurgical instruments and, more particularly, to preventing damage to a protective sleeve on a distal end of an electrosurgical instrument during installation of the protective sleeve, and further to devices used to ease assembly and removal of the protective sleeve.

Figure 1:
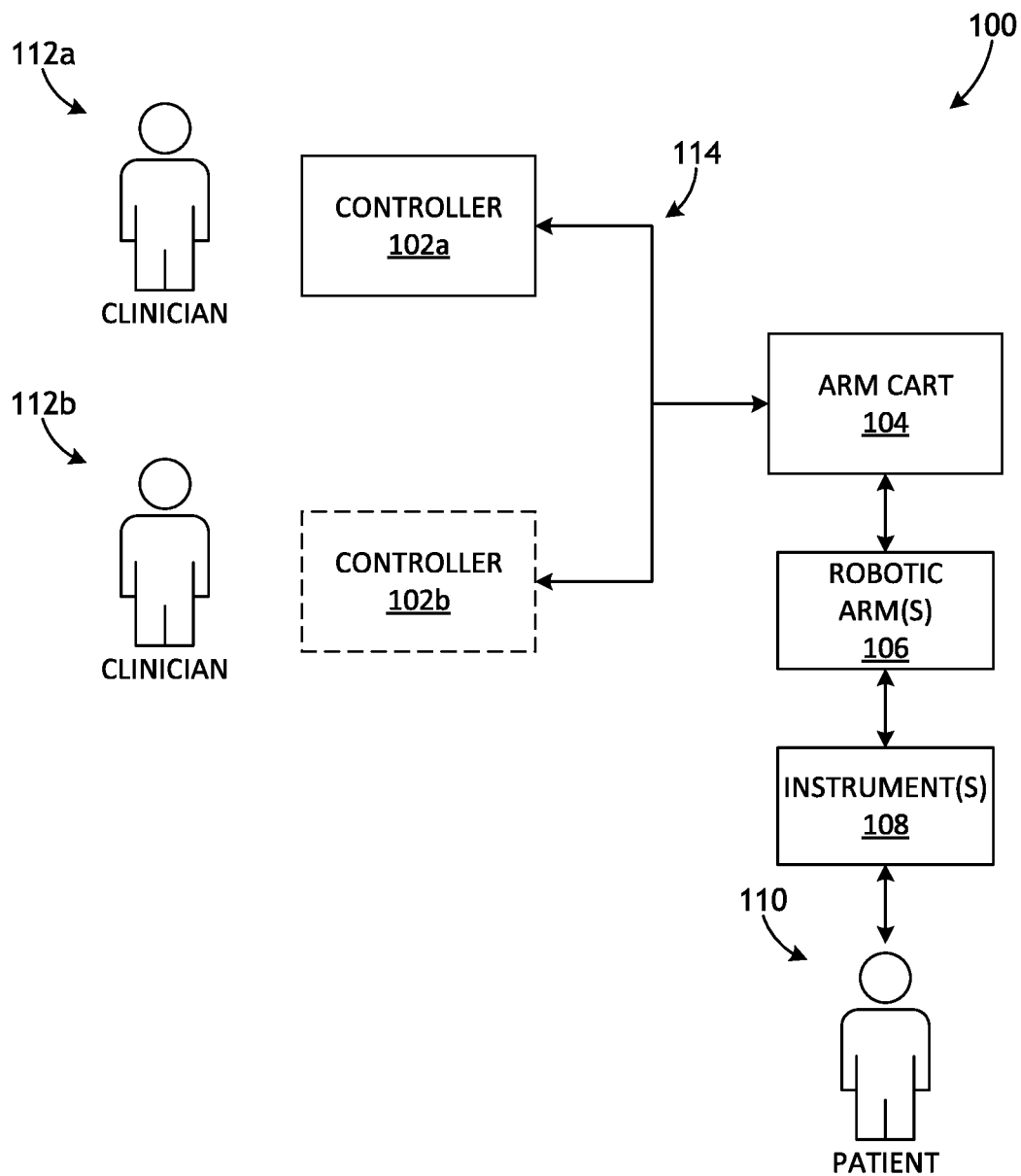
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104, although the arm cart 104 is not necessarily required. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a, b may control different robotic arms 106 or, in some cases, complete control of the robotic arms 106 may be passed between the clinicians 102a, b. In some embodiments, additional arm carts (not shown) having additional robotic arms (not shown) may be utilized during surgery on a patient 110, and these additional robotic arms may be controlled by one or more of the master controllers 102a, b.

The arm cart 104 and the master controllers 102a, b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The master controllers 102a, b generally include one or more physical controllers that can be grasped by the clinicians 112a, b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a, b can also include an optional feedback meter viewable by the clinicians 112a, b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
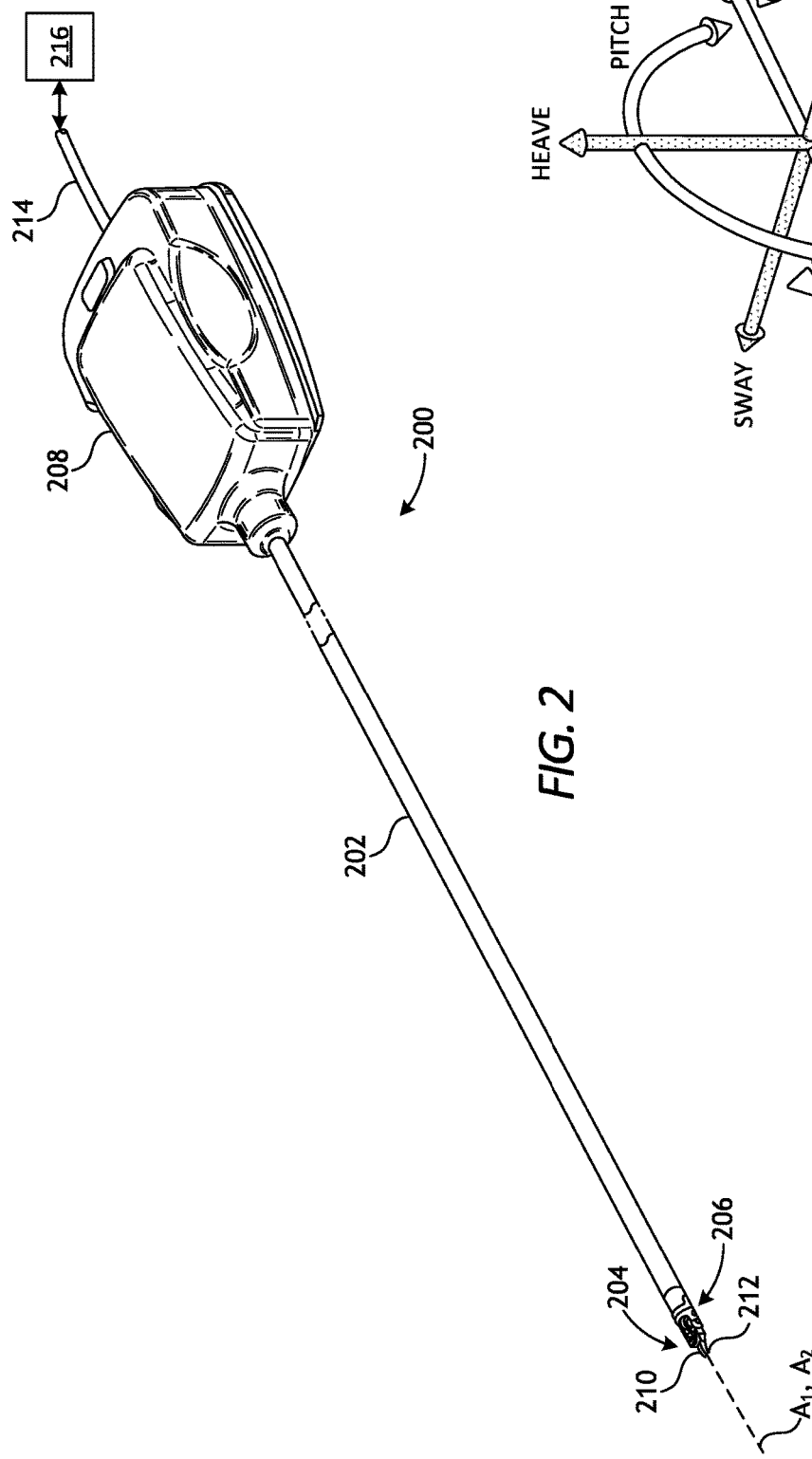
FIG. 2 is a side view of an example surgical tool that may incorporate some or all of the principles of the present disclosure.

FIG. 2 is side view of an example surgical tool 200 that may incorporate some or all of the principles of the present disclosure. The surgical tool 200 may be the same as or similar to the surgical instrument(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. The housing 208 includes (contains) various mechanisms designed to control operation of various features associated with the end effector 204 (e.g., clamping, firing, rotation, articulation, energy delivery, etc.). In at least some embodiments, the shaft 202, and hence the end effector 204 coupled thereto, is configured to rotate about a longitudinal axis $A_1$ of the shaft 202. In such embodiments, at least one of the mechanisms included (housed) in the housing 208 is configured to control rotational movement of the shaft 202 about the longitudinal axis $A_1$.

The surgical tool 200 can have any of a variety of configurations capable of performing at least one surgical function. For example, the surgical tool 200 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can have a variety of sizes, shapes, and configurations. In the illustrated embodiment, the end effector 204 comprises surgical scissors that include opposing jaws 210, 212 (alternately referred to as "blades")

configured to move (articulate) between open and closed positions. As will be appreciated, however, the opposing jaws 210, 212 may alternatively form part of other types of end effectors such as, but not limited to, a tissue grasper, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot at the wrist 206 to articulate the end effector 204 between the open and closed positions.

Figure 3:
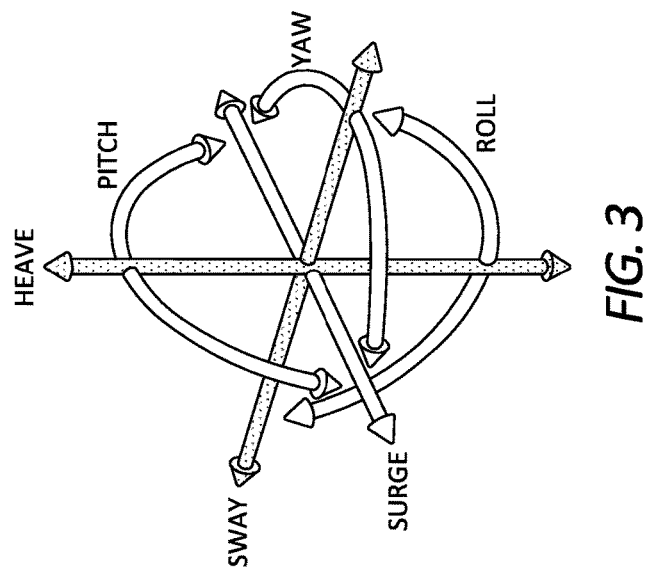
FIG. 3 illustrates potential degrees of freedom in which the wrist of FIG. 1 may be able to articulate (pivot).

FIG. 3 illustrates the potential degrees of freedom in which the wrist 206 may be able to articulate (pivot). The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 204) with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate movement and articulation of the end effector 204 relative to the shaft 202. Moving (actuating) at least some of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Still referring to FIG. 2, in some embodiments, the surgical tool 200 may be supplied with electrical power (current) via a power cable 214 coupled (permanent or detachable) to the housing 208. In other embodiments, the power cable 214 may be omitted and electrical power may be supplied to the surgical tool 200 via an internal power source, such as one or more batteries or fuel cells. For purposes of the present description, however, it will be assumed that electrical power is provided to the surgical tool 200 via the power cable 214. In either case, the surgical tool 200 may alternatively be characterized and otherwise referred to herein as an "electrosurgical instrument" capable of providing electrical energy to the end effector 204.

The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return conductor located at the end effector 204 via the return conductor. In the case of a bipolar tool with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

Figure 4:
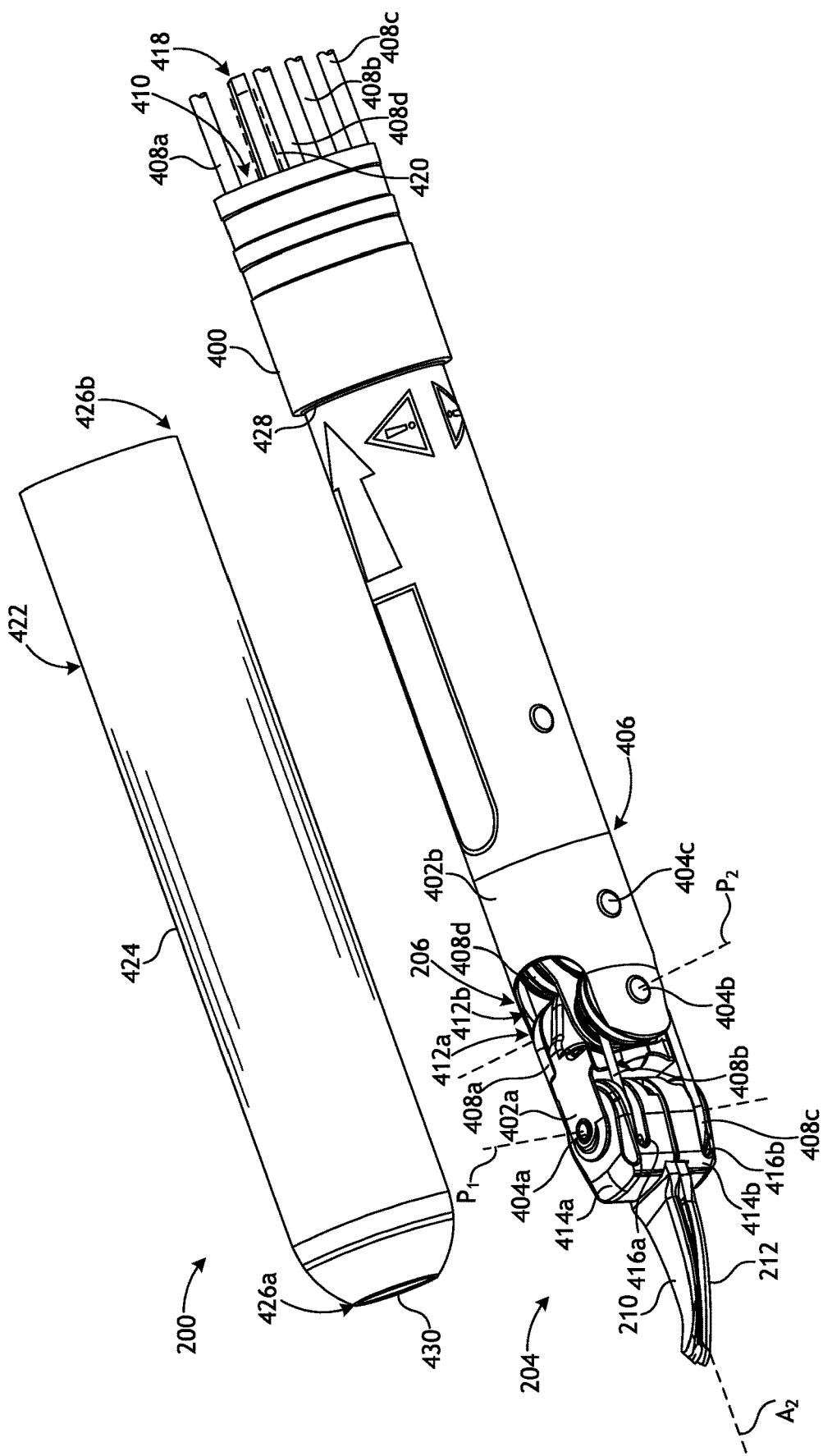
FIG. 4 is an enlarged isometric view of the distal end of the surgical tool of FIG. 1.

FIG. 4 is an enlarged isometric view of the distal end of the surgical tool 200 of FIG. 2. More specifically, FIG. 4 depicts enlarged views of the end effector 204 and the wrist 206, with the end effector 204 in the unarticulated position. The wrist 206 operatively couples the end effector 204 to the shaft 202 (FIG. 2). In the illustrated embodiment, however, a shaft adapter 400 may be directly coupled to the wrist 206 and otherwise interpose the shaft 202 and the wrist 206. In other embodiments, the shaft adapter 400 may be omitted and the shaft 202 may instead be directly coupled to the wrist 206, without departing from the scope of the disclosure. As used herein, the term "operatively couple" refers to a direct or indirect coupling engagement. Accordingly, the wrist 206 may be operatively coupled to the shaft 202 either through a direct coupling engagement where the wrist 206 is directly coupled to the distal end of the shaft 202, or an indirect coupling engagement where the shaft adapter 400 interposes the wrist 206 and the distal end of the shaft 202.

To operatively couple the end effector 204 to the shaft 202 (e.g., via the shaft adapter 400), the wrist 206 includes a distal clevis 402a and a proximal clevis 402b. The end effector 204 (i.e., the jaws 210, 212) is rotatably mounted to the distal clevis 402a at a first axle 404a, the distal clevis 402a is rotatably mounted to the proximal clevis 402b at a second axle 404b, and the proximal clevis 402b is coupled to a distal end 406 of the shaft adapter 400 (or alternatively the distal end of the shaft 202).

The wrist 206 provides a first pivot axis $P_1$ that extends through the first axle 404a and a second pivot axis $P_2$ that extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. In the illustrated embodiment, the jaws 210, 212 are mounted at the first pivot axis $P_1$, thereby allowing the jaws 210, 212 to pivot relative to each other to open and close the end effector 204 or alternatively pivot in tandem to articulate the orientation of the end effector 204.

A plurality of drive cables, shown as drive cables 408a, 408b, 408c, and 408d, extend longitudinally within a lumen 410 defined by the shaft adapter 400 (and/or the shaft 202 of FIG. 2) and pass through the wrist 206 to be operatively coupled to the end effector 204. While four drive cables 408a-d are depicted in FIG. 4, more or less than four drive cables 408a-d may be included, without departing from the scope of the disclosure.

The drive cables 408a-d form part of the cable driven motion system briefly described above, and may be referred to and otherwise characterized as cables, bands, lines, cords, wires, ropes, strings, twisted strings, elongate members, etc. The drive cables 408a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 410 can be a single lumen, as illustrated, or can alternatively comprise a plurality of independent lumens that each receive one or more of the drive cables 408a-d.

The drive cables 408a-d extend proximally from the end effector 204 to the drive housing 208 (FIG. 2) where they are operatively coupled to various actuation mechanisms or devices housed (contained) therein to facilitate longitudinal movement (translation) of the drive cables 408a-d within the lumen 410. Selective actuation of all or a portion of the drive cables 408a-d causes the end effector 204 (e.g., one or both of the jaws 210, 212) to articulate (pivot) relative to the shaft 202. More specifically, selective actuation causes a corresponding drive cable 408a-d to translate longitudinally within the lumen 410 and thereby cause pivoting movement of the end effector 204. One or more drive cables 408a-d, for example, may translate longitudinally to cause the end effector 204 to articulate (e.g., both of the jaws 210, 212 angled in a same direction), to cause the end effector 204 to open (e.g., one or both of the jaws 210, 212 move away from the other), or to cause the end effector 204 to close (e.g., one or both of the jaws 210, 212 move toward the other).

Moving the drive cables 408a-d can be accomplished in a variety of ways, such as by triggering an associated actuator or mechanism operatively coupled to or housed within the drive housing 208 (FIG. 2). Moving a given drive cable 408a-d constitutes applying tension (i.e., pull force) to the given drive cable 408a-d in a proximal direction, which causes the given drive cable 408a-d to translate and thereby cause the end effector 204 to move (articulate) relative to the shaft 202.

The wrist 206 includes a first plurality of pulleys 412a and a second plurality of pulleys 412b, each configured to interact with and redirect the drive cables 408a-d for engagement with the end effector 204. The first plurality of pulleys 412a is mounted to the proximal clevis 402b at the second axle 404b and the second plurality of pulleys 412b is also mounted to the proximal clevis 402b but at a third axle 404c located proximal to the second axle 404b. The first and second pluralities of pulleys 412a, b cooperatively redirect the drive cables 408a-d through an "S" shaped pathway before the drive cables 408a-d are operatively coupled to the end effector 204.

In at least one embodiment, one pair of drive cables 408a-d is operatively coupled to each jaw 210, 212 and configured to "antagonistically" operate the corresponding jaw 210, 212. In the illustrated embodiment, for example, the first and second drive cables 408a, b are coupled with a connector (not shown) at the first jaw 210, and the third and fourth drive cables 408c, d are coupled with a connector (not shown) at the second jaw 212. Consequently, actuation of the first drive cable 408a pivots the first jaw 210 about the first pivot axis $P_1$ toward the open position, and actuation of the second drive cable 408b pivots the first jaw 210 about the first pivot axis $P_1$ in the opposite direction and toward the closed position. Similarly, actuation of the third drive cable 408c pivots the second jaw 212 about the first pivot axis $P_1$ toward the open position, while actuation of the fourth drive cable 408d pivots the second jaw 212 about the first pivot axis $P_1$ in the opposite direction and toward the closed position.

Accordingly, the drive cables 408a-d may be characterized or otherwise referred to as "antagonistic" cables that cooperatively (yet antagonistically) operate to cause relative or tandem movement of the first and second jaws 210, 212. When the first drive cable 408a is actuated (moved), the second drive cable 408b naturally follows as coupled to the first drive cable 408a, and when the third drive cable 408c is actuated, the fourth drive cable 408d naturally follows as coupled to the third drive cable 408c, and vice versa.

The end effector 204 further includes a first jaw holder 414a and a second jaw holder 414b laterally offset from the first jaw holder 414a. The first jaw holder 414a is mounted to the first axle 404a and configured to receive and seat the first jaw 210 such that movement (rotation) of the first jaw holder 414a about the first pivot axis $P_1$ correspondingly moves (rotates) the first jaw 210. The first jaw holder 414a may also provide and otherwise define a first pulley 416a configured to receive and seat one or more drive cables, such as the first and second drive cables 408a, b to effect such movement (rotation). The second jaw holder 414b is similarly mounted to the first axle 404a and is configured to receive and seat the second jaw 212 such that movement (rotation) of the second jaw holder 414b about the first pivot axis $P_1$ correspondingly moves (rotates) the second jaw 212. The second jaw holder 414b may also provide and otherwise define a second pulley 416b configured to receive and seat one or more drive cables, such as the third and fourth drive cables 408c, d, to effect such movement (rotation).

The term "jaw holder," as used herein, is intended to apply to a variety of types of end effectors having opposing jaws or blades that are movable relative to one another. In the illustrated embodiment, the jaws 210, 212 comprise opposing scissor blades of a surgical scissors end effector. Accordingly, the jaw holders 414a, b may alternately be referred to as "blade holders". In other embodiments, however, the jaws 210, 212 may alternatively comprise opposing jaws used in a grasper end effector, or the like, and the term "jaw holder" similarly applies, without departing from the scope of the disclosure. Moreover, the term "holder" in "jaw holder" may be replaced with "mount," "drive member," or "actuation member."

The surgical tool 200 may also include an electrical conductor 418 that supplies electrical energy to the end effector 204, thereby converting the surgical tool 200 into an "electrosurgical instrument". Similar to the drive cables 408a-d, the electrical conductor 418 may extend longitudinally within the lumen 410. In some embodiments, the electrical conductor 418 and the power cable 214 (FIG. 2) may comprise the same structure. In other embodiments, however, the electrical conductor 418 may be electrically coupled to the power cable 214, such as at the drive housing 208 (FIG. 2). In yet other embodiments, the electrical conductor 418 may extend to the drive housing 208 where it is electrically coupled to an internal power source, such as batteries or fuel cells.

In some embodiments, the electrical conductor 418 may comprise a wire. In other embodiments, however, the electrical conductor 418 may comprise a rigid or semi-rigid shaft, rod, or strip (ribbon) made of a conductive material. In some embodiments, the electrical conductor 418 may be partially covered with an insulative covering 420 (shown in dashed lines) made of a non-conductive material. The insulative covering 420, for example, may comprise a plastic applied to the electrical conductor 418 via heat shrinking, but could alternatively be any other non-conductive material.

In operation, the end effector 204 may be configured for monopolar or bipolar operation, without departing from the scope of the disclosure. Electrical energy is transmitted by the electrical conductor 418 to the end effector 204, which acts as an active (or source) electrode. In at least one embodiment, the electrical energy conducted through the electrical conductor 418 may comprise radio frequency ("RF") energy exhibiting a frequency between about 100 kHz and 1 MHz. The RF energy causes ultrasonic agitation or friction, in effect resistive heating, thereby increasing the temperature of target tissue. Accordingly, electrical energy supplied to the end effector 204 is converted to heat and transferred to adjacent tissue to cut, cauterize, and/or coagulate the tissue (dependent upon the localized heating of the tissue), and thus may be particularly useful for sealing blood vessels or diffusing bleeding.

The surgical tool 200 may further include a protective sleeve 422 configured to insulate various live (energized) portions of the end effector 204 (including the wrist 206), and thereby protect the patient from stray electrical discharge during operation. As illustrated, the sleeve 422 may comprise an elongate and generally cylindrical body 424 having a first or distal end 426a and a second or proximal end 426b opposite the distal end 426a. The body 424 may be sized to extend over portions of the end effector 204, the wrist 206, and the shaft adapter 400 (or alternatively the shaft 202 when the shaft adapter 400 is omitted). When the sleeve 422 is properly positioned for use, the jaw members 210, 212 protrude out an aperture 430 defined in the distal end 426a of the body 424 and the proximal end 426b engages or comes into close contact with a radial shoulder 428 (alternately referred to as a "shaft adapter flange") defined on the shaft adapter 400 (or the shaft 202). When the sleeve 422 is properly positioned (installed), electrical current can only be conducted to patient tissue as intended at the exposed jaw members 210, 212.

Figure 5:
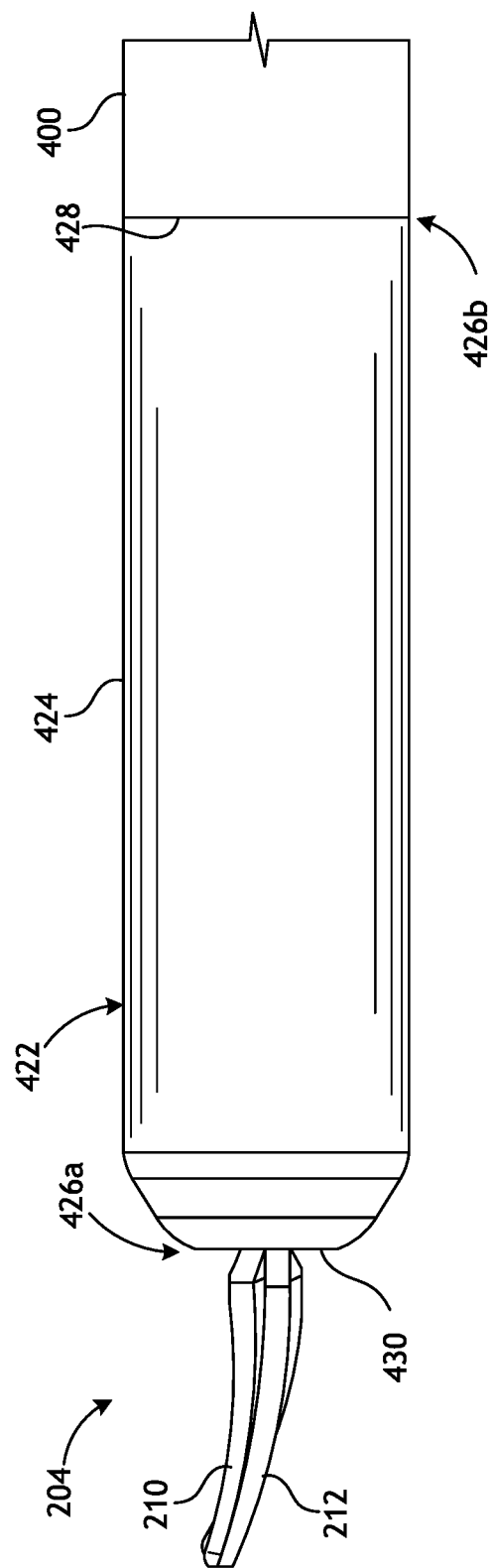
FIG. 5 is a side view of the sleeve assembled onto the end effector.

FIG. 5 is a side view of the sleeve 422 as assembled onto the end effector 204. As illustrated, the sleeve 422 is advanced proximally until the jaw members 210, 212 protrude out of the aperture 430 at the distal end 426a of the body 424 and the proximal end 426b engages the radial shoulder 428 of the shaft adapter 400 (or the shaft 202 of FIG. 2). The sleeve 422 may be assembled onto the end effector 204 within a sterile field before surgery and removed before cleaning the tool 200 (FIG. 2). The sleeve 422 must be properly installed to mitigate electrical discharge in unintended pathways, and the responsibility for proper installation is often left to the various scrub nurses on hand in an operating room. One challenge is error proofing proper installation of the sleeve 422 and ensuring that the sleeve 422 is properly positioned for use. While extending the sleeve 422 over the jaw members 210, 212, there is a risk that the jaw members 210, 212 may engage and cut into the inner wall of the sleeve 422, which could result in the creation of holes and subsequent inadvertent electrical discharge to the patient through the holes during use. The present disclosure includes embodiments that ensure proper assembly (installation) of the sleeve 422 while simultaneously preventing the jaw members 210, 212 from gouging the inner wall of the sleeve 422 during installation.

Moreover, the sleeve 422 may be made of a flexible material and installed via an interference fit between the inner radial surface of the sleeve 422 and the outer radial surfaces of the end effector 204, the wrist 206 (FIG. 4), and/or the shaft adapter 400. Suitable flexible materials include, but are not limited to, thermoplastic polyurethane (TPU), nitrile rubber, polyisoprene, silicone, or any combination thereof. The flexibility of the sleeve 422 allows the wrist 206 to articulate during use, but as the wrist 206 articulates, the sleeve 422 may have a tendency to creep axially, which can result in the proximal end 426b separating from the radial shoulder 428 and increasing the likelihood of electrical discharge in unintended pathways. Embodiments described herein also provide means for securing the sleeve 422 in position, and sleeve extraction tools that may be used to remove the sleeve 422.

Figure 6A:
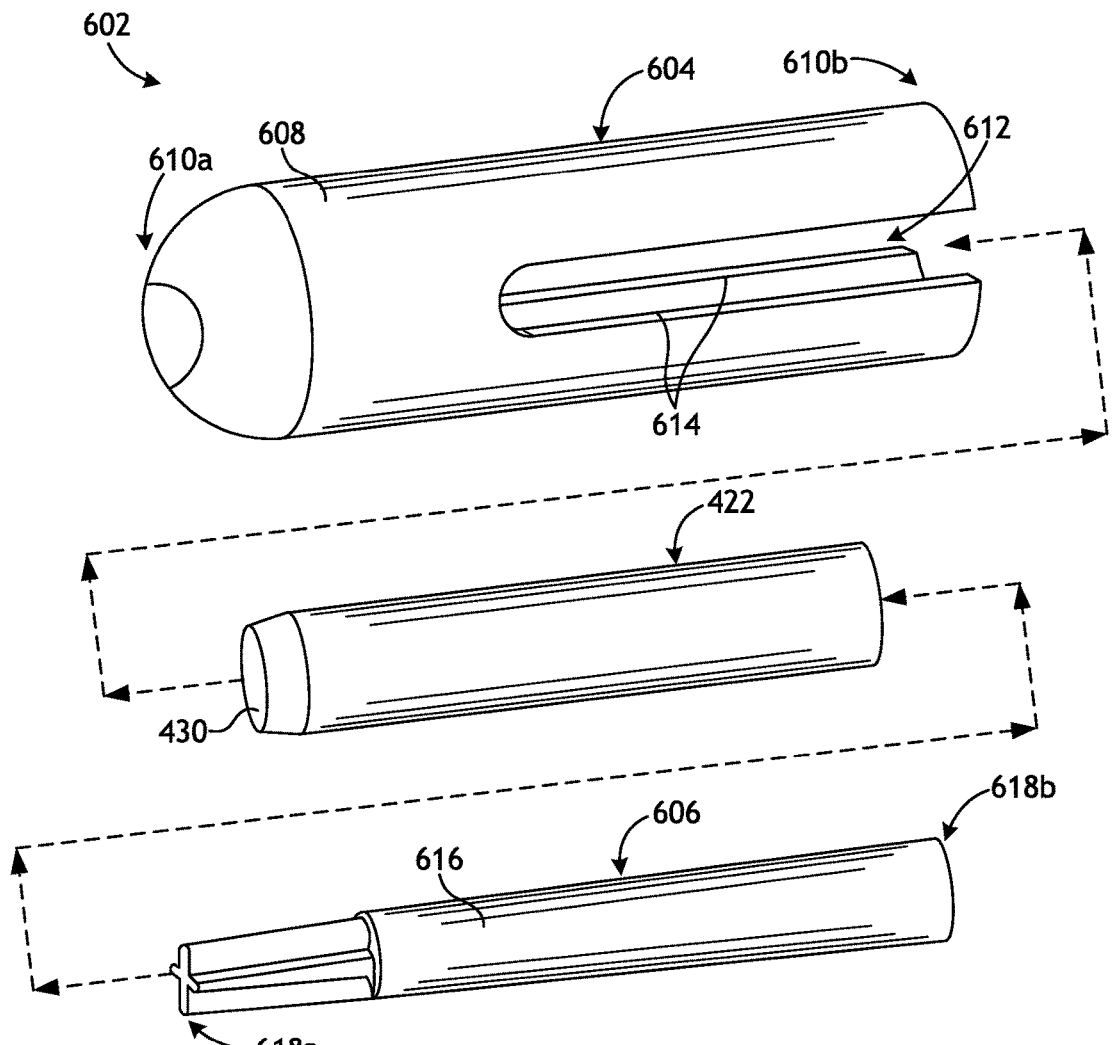
FIGS. 6A and 6B are exploded and cross-sectional side views, respectively, of an example sleeve insertion assembly that may be used in accordance with one or more principles of the present disclosure.
Figure 6B:
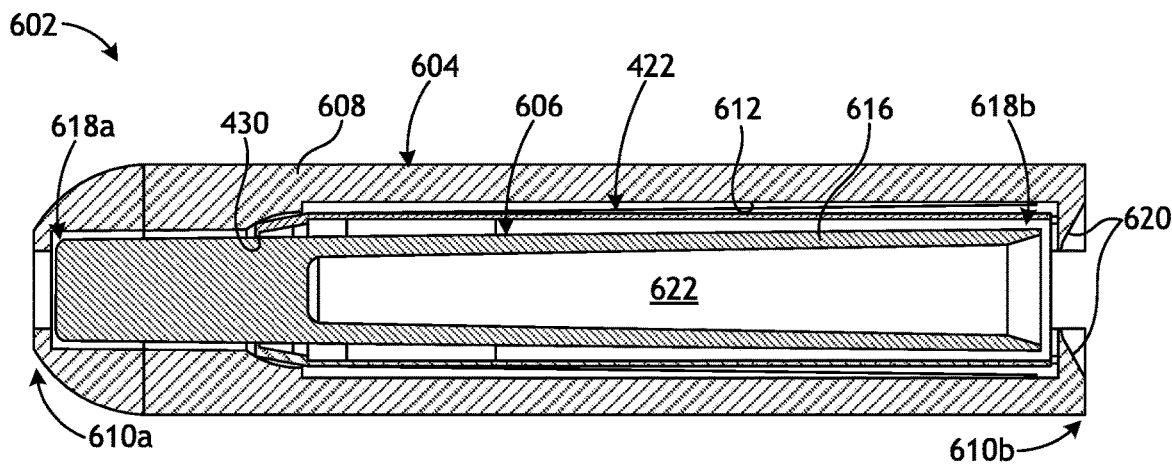

FIGS. 6A and 6B are exploded and cross-sectional side views, respectively, of an example sleeve insertion assembly 602 that may be used in accordance with one or more principles of the present disclosure. The sleeve insertion assembly 602 may be used to help install (assemble) the sleeve 422 on the end effector 204 (FIGS. 4-5) and simultaneously protect a user (e.g., a scrub nurse, surgeon, etc.) and the sleeve 422 from inadvertent accidental contact with the jaw members 210, 212 (FIGS. 4-5). As will be appreciated, the jaw members 210, 212 are required to be exceptionally sharp and the user is commonly tasked with assembling the sleeve 422 over the jaw members 210, 212. If proper precaution is not taken, the user may inadvertently cut or puncture the sleeve 422 and/or his/her hand(s) by coming into contact with the jaw members 210, 212. The sleeve insertion assembly 602 may prove advantageous in mitigating the occurrence of damage or cuts caused by accidental mishandling of the end effector 204.

As illustrated, the sleeve insertion assembly 602 includes a sleeve inserter 604, the sleeve 422, and a blade guard 606. The sleeve inserter 604 includes an elongate, generally cylindrical body 608 having a distal end 610a and a proximal end 610b opposite the distal end 610a. The body 608 may be made of a variety of materials including, but not limited to, plastic, metal, rubber, an elastomer, silicone, or any combination thereof.

The body 608 defines an inner chamber 612 large enough and otherwise sized to extend over and receive the sleeve 422. In some embodiments, the body 608 may define one or more longitudinal slots 614 (two shown) that extend from the proximal end 610b toward the distal end 610a. The slots 614 create weak points in the body 608 that allow a user to pinch and thereby collapse the body 608 against the outer radial surface of the sleeve 422 during installation. This allows the user to advance the sleeve 422 toward the installed position by gripping and moving the sleeve inserter 604 instead of directly contacting the outer surface of the sleeve 422.

While two slots 614 are shown in the illustrated embodiment, more or less than two may alternatively be employed. In some embodiments, as illustrated, one or more of the slots 614 may exhibit an axial length that is greater than half the overall length of the body 608. In other embodiments, the axial length of the slots 614 may be less than half the overall length of the body 608, without departing from the scope of the disclosure.

The blade guard 606 provides an elongate, generally cylindrical body 616 having a closed distal end 618a and an open proximal end 618b opposite the distal end 618a. The body 616 may be sized and otherwise configured to be received within the sleeve 422, and the distal end 618a may extend through the aperture 430 of the sleeve 422 when properly installed. Accordingly, the sleeve insertion assembly 602 forms a nested assembly where the blade guard 606 is received within the sleeve 422, and the sleeve 422 and the blade guard 606 are jointly received within the sleeve inserter 604.

In at least one embodiment, the sleeve inserter 604 may provide or otherwise define a retention mechanism 620 (FIG. 6B) at the proximal end 610b to help contain the sleeve 422 and the blade guard 606 within the sleeve inserter 604 and otherwise prevent them from falling out of the sleeve inserter 604. In some embodiments, as illustrated, the retention mechanism 620 may comprise a protrusion that extends a short distance into the inner chamber 612, but could alternatively comprise any other structural feature that helps maintain the sleeve 422 and the blade guard 606 within the sleeve inserter 604.

The blade guard 606 may define an interior 622 sized to receive the jaw members 210, 212 (FIGS. 4-5) when installing the sleeve 422 on the end effector 204 (FIGS. 4-5). The blade guard 606 may be configured to prevent the jaw members 210, 212 from piercing or otherwise engaging the inner wall of the sleeve 422 during installation of the sleeve 422. To accomplish this, the body 616 of the blade guard 606 may be made of a variety of rigid materials such as, but not limited to, a metal, a thermoplastic (e.g., acrylonitrile butadiene styrene, polycarbonate, polyether ether ketone, etc.), a composite material, and any combination thereof.

FIGS. 7A-7C are progressive cross-sectional side views of the sleeve insertion assembly 602 showing example installation of the sleeve 422, according to one or more embodiments. In FIG. 7A, the sleeve insertion assembly 602 has the blade guard 606 nested within the sleeve 422 and both are arranged within the sleeve inserter 604 and prepared to deploy the sleeve 422. In some embodiments, the sleeve inserter 604, the sleeve 422, and the blade guard 606 may be packaged in a common sterile packaging and shipped together. Upon opening the sterile pack, a user (e.g., a scrub nurse, surgeon, etc.) may mate the sleeve 422 and the blade guard 606, as generally described above, and extend the nested sleeve 422 and blade guard 606 into the sleeve inserter 604. In other embodiments, however, the sleeve 422 and the blade guard 606 may be pre-assembled into the sleeve inserter 604 upon delivery.

To deploy the sleeve 422, the sleeve insertion assembly 602 is brought into proximity of the end effector 204 and the jaw members 210, 212 are aligned with and inserted into the interior 622 of the blade guard 606. In some embodiments, the opening of the blade guard 606 at the proximal end 618b may be tapered or otherwise angled to help receive the jaw members 210, 212 without binding against sharp corners. Inserting the jaw members 210, 212 within the blade guard 606 prevents the jaw members 210, 212 from inadvertently contacting and potentially cutting the inner wall of the sleeve 422. The user may then advance the sleeve inserter 604 proximally relative to the end effector 204 and simultaneously advance the sleeve 422 over the end effector 204, the wrist 206, and the shaft adapter 400 (or the shaft 202 of FIG. 2).

The opening of the blade guard 606 at the proximal end 618b is large enough to receive the jaw members 210, 212, but smaller than the body of the end effector 204 (i.e., the jaw holders 414a, b of FIG. 4). Consequently, the entire end effector 204 is prevented from entering the interior 622. Instead, as the sleeve inserter 604 is advanced proximally relative to the end effector 204 (i.e., to the right in FIGS. 7A-7C), portions of the end effector 204 will engage the proximal end 618b of the blade guard 606 and further proximal movement of the sleeve inserter 604 will correspondingly urge the blade guard 606 distally relative to the sleeve 422 and the sleeve inserter 604.

In FIG. 7B, the sleeve inserter 604 has moved further in the proximal direction relative to the end effector 204. In some embodiments, the sleeve 422 may be advanced over the end effector 204 by applying an opposing radial load F on the sleeve inserter 604 at or near the proximal end 610b, such as by pinching the sleeve inserter 604 with the thumb and index fingers of one hand. The radial load F may cause the inner radial surface of the sleeve inserter 604 to engage and otherwise grip the outer radial surface of the sleeve 422. In some embodiments, the inner radial surface at or near the proximal end 610b may include a gripping interface, such as a knurled surface or a ribbed contour, configured to help grip the outer radial surface of the sleeve 422. The slots 614 (FIG. 6A) allow the sleeve inserter 604 to flex radially inward, and the sleeve inserter 604 may then be advanced proximally relative to the end effector 204 without potentially binding (crumpling) the sleeve 422 within the sleeve inserter 604. Alternatively, the inside of the sleeve inserter 604 may be larger than the outer diameter of the sleeve 422 such that the user can push the sleeve 422 on by gripping the distal end of the sleeve inserter 604. This clearance between the inside surface of the sleeve inserter 604 and the sleeve 422 may be 0.05 mm to 1.0 mm, for example. This clearance prevents pinching of the sleeve 422 against the shaft adapter 400 and at the same time contains the sleeve 422 enough to prevent buckling of the sleeve 422 during assembly of the sleeve 422.

As the sleeve inserter 604 moves proximally relative to the end effector 204, the blade guard 606 may correspondingly move distally relative to the sleeve 422 as engaged against the end effector 204 at the distal end 618a. The sleeve inserter 604 may define or otherwise provide an aperture 702 at the distal end 610a, and the distal end 618a of the blade guard 606 may extend through the aperture 702 as the blade guard 606 moves distally. The sleeve inserter 604 may be made of a flexible material that allows the aperture 702 to flex and expand radially outward to receive the blade guard 606 as it advances through the aperture 702.

In FIG. 7C, the sleeve inserter 604 is advanced proximally relative to the end effector 204 until the sleeve 422 is properly installed over the end effector 204, the wrist 206, and the shaft adapter 400 (or the shaft 202 of FIG. 2). In some embodiments, the sleeve inserter 604 is advanced proximally until the proximal end 426b of the sleeve 422 engages or comes into close contact with the radial shoulder 428 of the shaft adapter 400 (or the shaft 202 of FIG. 2). In other embodiments, or in addition thereto, the sleeve inserter 604 may be advanced proximally until the end effector 204 bottoms out, at which point the sleeve 422 will be properly seated against the radial shoulder 428. More specifically, when the sleeve 422 is pushed up against the radial shoulder 428, the sleeve inserter 604 presents a hard stop such that the sleeve inserter 604 cannot be pushed proximally any more. This prevents the sleeve 422 from being pushed too far proximally on the shaft adapter 400 and possibly over the radial shoulder 428. In at least one embodiment, for example, this end of travel hard stop can be provided by a proximal portion of the blade guard 606 engaging the inner distal diameter of the sleeve inserter 604.

The sleeve inserter 604 may then be retracted distally to thereby remove the sleeve inserter 604 from the end effector 204 and leave the sleeve 422 properly installed. In embodiments where the sleeve inserter 604 is made of a pliable material (e.g., an elastomer or silicone), the slots 614 (FIG. 6A) may allow the sleeve inserter 604 to be "peeled away" from the end effector 204 after assembly. In such embodiments, the user may grasp the sleeve inserter 604 at or near the proximal end 610b and the slots 614 may help progressively detach the sleeve inserter 604 similar to how a banana is peeled.

In some embodiments, the blade guard 606 may be removed from the aperture 702 by the user, but may alternatively be left engaged with the sleeve inserter 604 at the aperture 702. In some embodiments, the blade guard 606 may be manufactured or otherwise fabricated of a color that is readily perceivable by a user (e.g., a scrub nurse, surgeon, etc.), such as bright or fluorescent orange. In at least one embodiment, one or more visual indicators (not shown) may be included on the body of the blade guard 606. Once the visual indicator(s) is exposed, that may be an indication to the user that the sleeve 422 is properly seated.

In some embodiments, the sleeve inserter 604 may also be used to help remove the sleeve 422. In such embodiments, the sleeve inserter 604 may be extended over the sleeve 422, and the radial load F (FIG. 7B) may again be applied to engage and otherwise grip the outer radial surface of the sleeve 422 at or near the proximal end 426b. Once the sleeve 422 is engaged, the user may move the sleeve inserter 604 and the sleeve 422 distally together relative to the end effector 204. In such embodiments, the gripping interface mentioned above may prove advantageous to help grip the outer radial surface of the sleeve 422.

Figure 8:
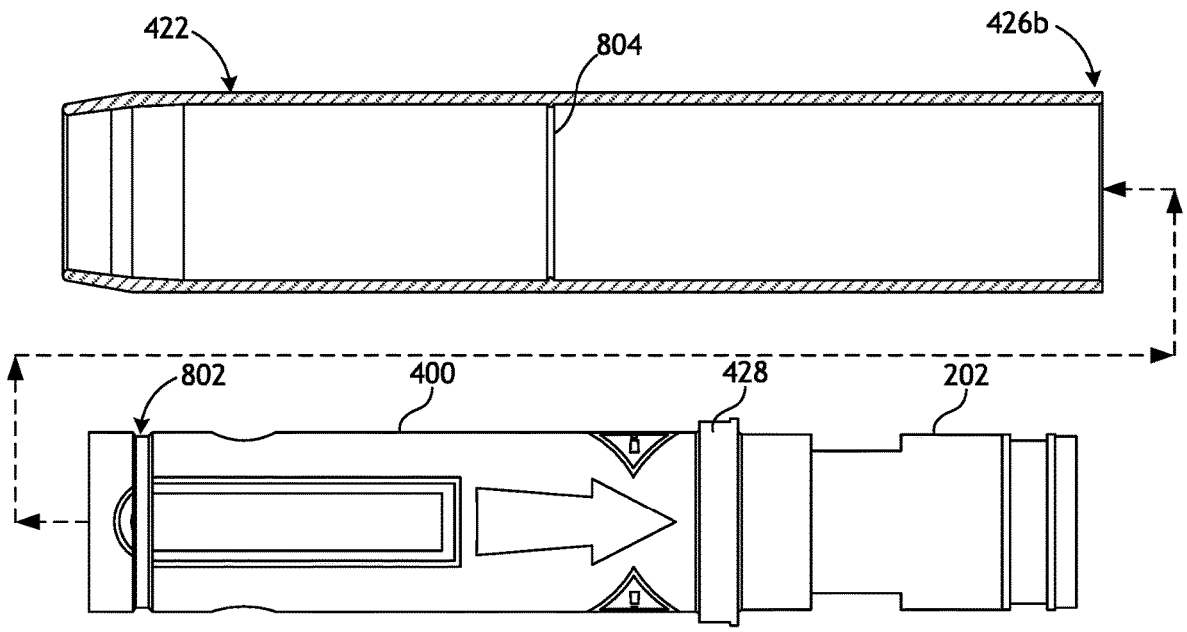
FIG. 8 is a partial cross-sectional view of the sleeve and the shaft adapter of FIGS. 4-5.

FIG. 8 is an exploded, partial cross-sectional view of the sleeve 422 and the shaft adapter 400, according to one or more embodiments of the disclosure. The flexibility of the sleeve 422 allows the wrist 206 (FIGS. 2 and 4) to articulate during use, but as the wrist 206 articulates, the sleeve 422 may have a tendency to creep axially, which can result in the proximal end 426b of the sleeve 422 separating from the radial shoulder 428 and increasing the likelihood of electrical discharge in unintended pathways. In some embodiments, as illustrated, the shaft adapter 400 may provide or otherwise define one or more annular grooves 802 on its outer surface, and the inner surface of the sleeve 422 may provide or otherwise define a corresponding one or more annular protrusions 804 (two shown) configured to mate with the annular grooves 802. The sleeve 422 may be advanced proximally until the protrusions 804 locate and snap into engagement with the grooves 802, which helps maintain the sleeve 422 in position during use but also provides a positive indicator that the sleeve 422 is properly installed.

In some embodiments, the groove 802 and the protrusion 804 may be spaced from the radial shoulder 428 and the proximal end 426b, respectively, by known distances such that when the protrusion 804 locates the groove 802, the proximal end 426b of the sleeve 422 may simultaneously engage (or come into close contact with) the radial shoulder 428. Moreover, it should be noted that while FIG. 8 depicts the sleeve 422 being secured to the shaft adapter 400, the sleeve 422 may alternatively be coupled to the shaft 202 via similar engagement means, without departing from the scope of the disclosure. Furthermore, the placement of the groove 802 and the protrusion 804 may be reversed, where the groove 802 is alternatively defined on the sleeve 422 and the protrusion 804 is defined on the shaft adapter 400 (or the shaft 202), without departing from the scope of the disclosure.

Figure 9A:
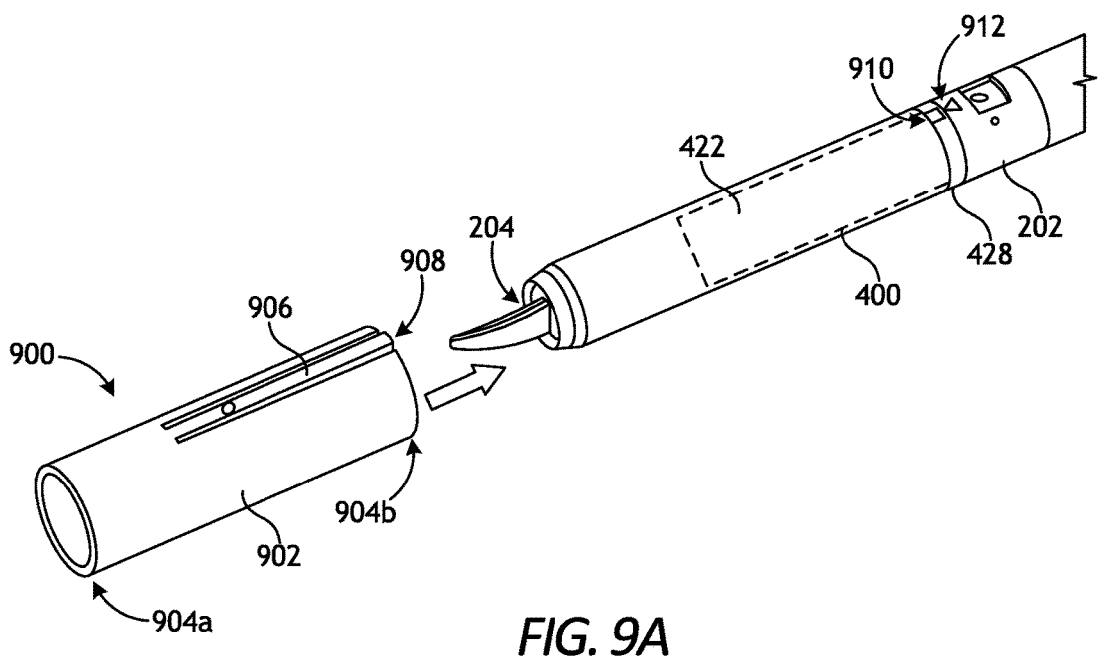
FIGS. 9A and 9B are isometric and side views, respectively, of an example sleeve extractor, according to one or more embodiments.
Figure 9B:
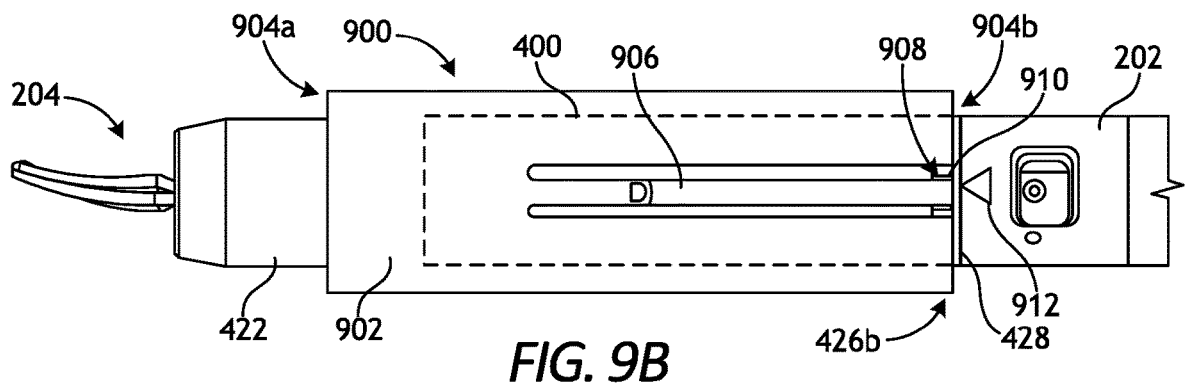

FIGS. 9A and 9B are isometric and side views, respectively, of an example sleeve extractor 900, according to one or more embodiments. The sleeve extractor 900 may be designed and used to remove the sleeve 422 from the end effector 204 following use. As illustrated, the sleeve extractor 900 has a generally cylindrical body 902 having a distal end 904a and a proximal end 904b. The proximal end 904b may be open to receive the end effector 204 and the sleeve 422.

The sleeve extractor 900 may be capable of engaging the proximal end 426b of the sleeve 422 such that the user does not have to grab (grip) the outer radial surface of the sleeve 422 or pull on the distal end 426a of the sleeve 422 for removal. To accomplish this, the sleeve extractor 900 may provide or otherwise define one or more longitudinally-extending fingers 906 configured to engage the proximal end 426b of the sleeve 422. Each finger 906 may provide a tab 908 that extends radially inward and is sized to be received within a notch 910 defined in the shaft adapter 400 (or the shaft 202 of FIG. 2). In at least one embodiment, as illustrated, the notch 910 may be defined in the radial shoulder 428, which may comprise a shaft adapter ring configured to help secure the shaft adapter 400 to the shaft 202. The notch 910 may be located proximal to the proximal end 426b of the sleeve 422 when the sleeve 422 is properly installed.

To remove the sleeve 422, the sleeve extractor 900 is advanced over the end effector 204 and the sleeve 422. The sleeve extractor 900 may be advanced proximally and rotated relative to the sleeve 422 until the tab 908 of the finger 906 angularly and axially locates the notch 910. In at least one embodiment, as illustrated, a marking 912 (e.g., an arrow or the like) may be provided on the shaft adapter 400 (or the shaft 202 of FIG. 2) to help the user accurately locate the notch 910. The marking 912 may be laser etched or painted onto the outer surface, or may alternatively comprise a sticker adhered thereto in the proper location.

Once the notch 910 is located, the user may provide a radial inward load on the finger 906 to seat (receive) the tab 908 within the notch 910 and thereby place the tab 908 at the proximal end 426b of the sleeve 422. The sleeve extractor 900 may then be retracted distally relative to the shaft adapter 400 and the tab 908 may engage the proximal end 426b and urge the sleeve 422 in the same direction. Continued distal movement of the sleeve extractor 900 will eventually remove the sleeve 422 from the shaft adapter 400 and the end effector 204.

While the sleeve extractor 900 is depicted in FIGS. 9A-9B as having an open distal end 904a, it is contemplated herein to have a closed distal end 904a. A closed distal end 904a may prevent the jaw members 210, 212 of the end effector 204 from extending out of the distal end 904a, which thereby prevents the jaw members 210, 212 from contacting the user during use of the sleeve extractor 900. Moreover, the closed distal end 904a may also serve to contain the sleeve 422 inside its cylindrical body after removal of the sleeve 422 for easy disposal of the sleeve 422 and the sleeve extractor 900 together.

Figure 10A:
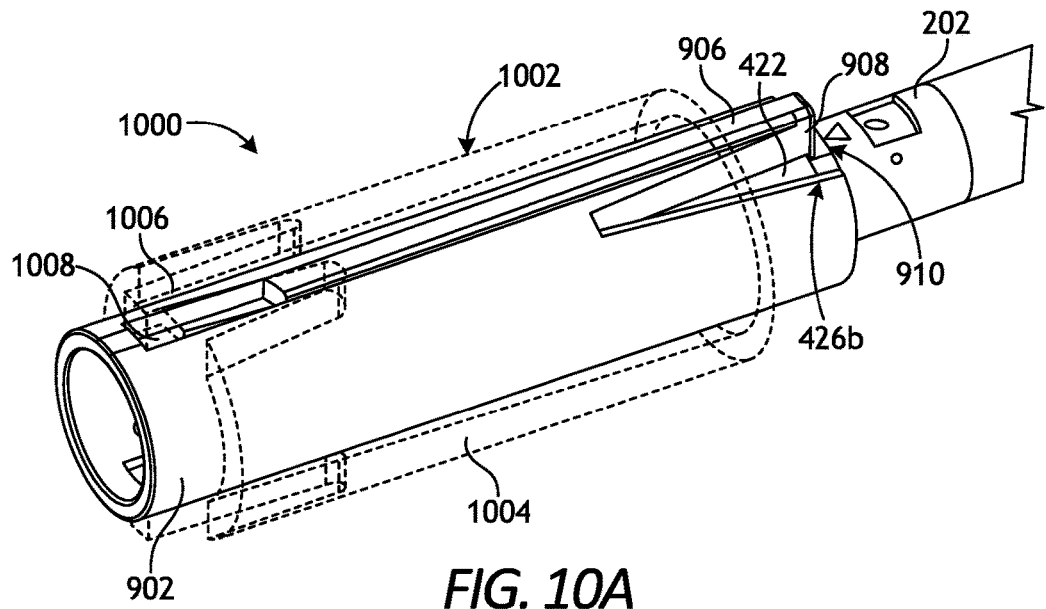
FIGS. 10A and 10B are isometric and side views, respectively, of another example sleeve extractor, according to one or more embodiments.
Figure 10B:
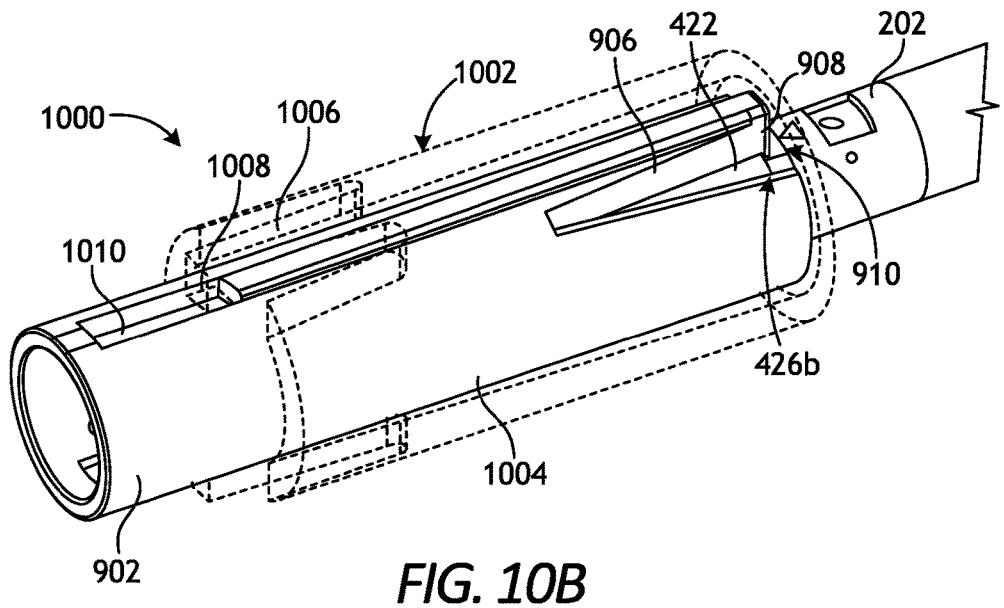

FIGS. 10A and 10B are isometric and side views, respectively, of another example sleeve extractor 1000, according to one or more embodiments. The sleeve extractor 1000 may be similar in some respects to the sleeve extractor 900 of FIGS. 9A-9B and therefore may be best understood with reference thereto, where like numerals correspond to similar components not described again. As illustrated, the sleeve extractor 1000 includes the body 902 that defines the longitudinally-extending finger(s) 906 configured to engage the proximal end 426b of the sleeve 422 with the tab 908 when the tab 908 is received within the notch 910.

The sleeve extractor 1000 may further include a cylindrical lock 1002 that provides a generally cylindrical body 1004 capable of extending about the body 902. The cylindrical lock 1002 may provide or define a locking arm 1006 that provides an extension 1008 receivable within a slot 1010 defined on the body 902. The cylindrical lock 1002 may be able to translate axially relative to the sleeve extractor 1000, and the extension 1008 received within the slot 1010 prevents the cylindrical lock 1002 from moving beyond the confines of the slot 1010.

To remove the sleeve 422, the sleeve extractor 1000 with the cylindrical lock 1002 positioned thereabout are advanced over the end effector 204 and the sleeve 422. The sleeve extractor 1000 may be advanced proximally and rotated relative to the sleeve 422 until the tab 908 of the finger 906 angularly and axially locates the notch 910. Once the notch 910 is located, the cylindrical lock 1002 may be advanced proximally relative to the underlying body 902, as shown in FIG. 10B. Proximal movement of the cylindrical lock 1002 will be limited by the axial length of the slot 1010 and the extension 1008 received therein.

Advancing the cylindrical lock 1002 proximally acts on the finger 906 and forces the tab 908 into engagement with the notch 910, which places the tab 908 at the proximal end 426b of the sleeve 422. In some embodiments, for instance, one or both of the inner radial surface of the cylindrical lock 1002 and the outer radial surface of the finger 906 may be tapered or otherwise angled such that the finger 906 is urged radially inward as the cylindrical lock 1002 advances. Alternatively, the finger 906 may be naturally biased away from the sleeve 422, and advancing the cylindrical lock 1002 proximally acts on the finger 906 and forces the arm 906 radially inward.

Once the tab 908 is seated within the notch 910, the sleeve 422 may be removed by retracting the sleeve extractor 1000 distally relative to the shaft adapter 400. As the sleeve extractor 1000 moves distally, the tab 908 may engage the proximal end 426b of the sleeve 422 and simultaneously urge the sleeve 422 in the same direction. Continued distal movement of the sleeve extractor 1000 will eventually remove the sleeve 422 from the shaft adapter 400 and the end effector 204.

While the sleeve extractor 1000 is depicted in FIGS. 10A-10B as having an open distal end, it is contemplated herein to have a closed distal end for the same reasons mentioned above for the sleeve extractor 900 of FIGS. 9A-9B.

Figure 11A:
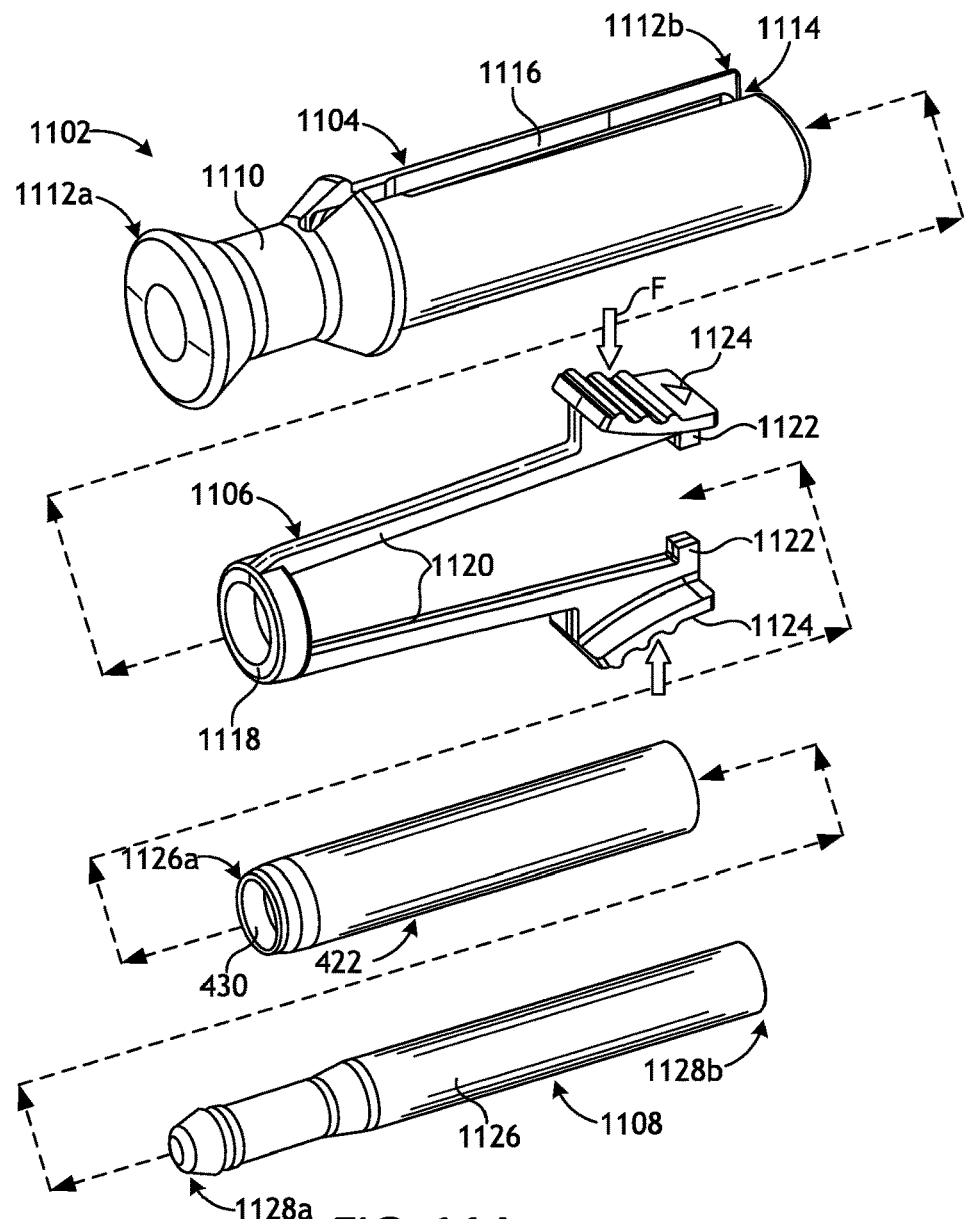
FIGS. 11A and 11B are isometric exploded and assembled views, respectively, of another example sleeve insertion assembly that may be used in accordance with one or more principles of the present disclosure.
Figure 11B:
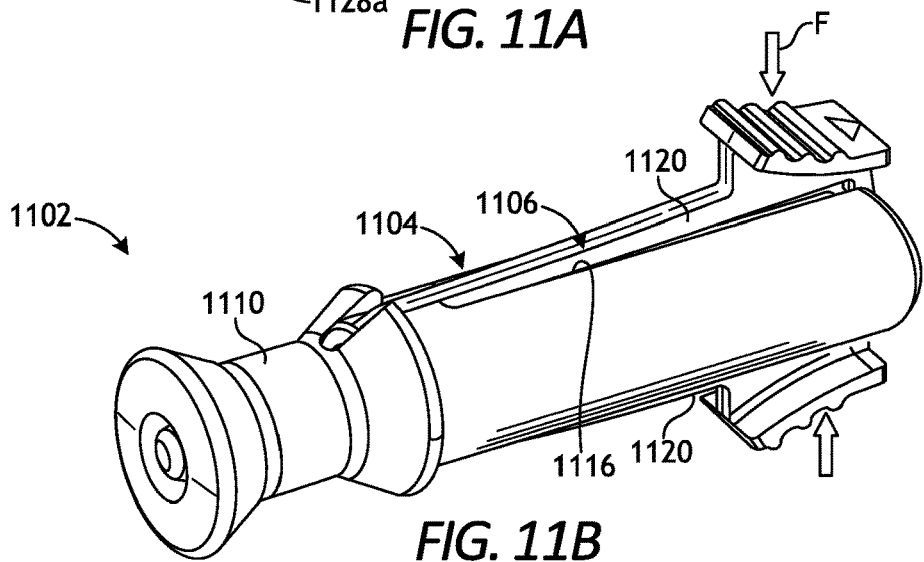

FIGS. 11A and 11B are isometric exploded and assembled views, respectively, of another example sleeve insertion assembly 1102 that may be used in accordance with the principles of the present disclosure. The sleeve insertion assembly 1102 may be similar in some respects to the sleeve insertion assembly 602 of FIGS. 6A-6B and therefore may be used to help install (assemble) the sleeve 422 on the end effector 204 (FIGS. 4-5) and simultaneously protect the sleeve 422 from inadvertent accidental contact with the jaw members 210, 212 (FIGS. 4-5).

As illustrated, the sleeve insertion assembly 1102 includes a sleeve inserter 1104, a sleeve extraction tool 1106, the sleeve 422, and a blade guard 1108. The sleeve inserter 1104 includes an elongate, generally cylindrical body 1110 having a distal end 1112a and a proximal end 1112b opposite the distal end 1112a. The body 1110 may be made of a variety of materials including, but not limited to, plastic, metal, rubber, an elastomer, silicone, and any combination thereof. In at least one embodiment, however, the body 1110 will be made of a flexible material, such as silicone or a pliable elastomer that allows the body to flex or expand during use.

The body 1110 defines an inner chamber 1114 large enough and otherwise sized to extend over and receive the sleeve 422 and portions of the sleeve extraction tool 1106. The body 1110 may define one or more longitudinal slots 1116 (one shown) that extend from the proximal end 1112b toward the distal end 1112a. The slots 1116 allow the sleeve inserter 1104 to flex outward upon receiving the end effector 204 (FIGS. 4-5), as described below.

The sleeve extraction tool 1106 may be made of a rigid or semi rigid material, such as a thermoplastic or a metal. As illustrated, the sleeve extraction tool 1106 provides an annular ring 1118 and one or more arms 1120 (two shown) that extend longitudinally from the ring 1118. When the sleeve insertion assembly 1102 is properly assembled, the ring 1118 may be received within the inner chamber 1114 of the sleeve inserter 1104, and each arm 1120 may be received within a corresponding one of the longitudinal slots 1116.

Each arm 1120 may provide a tab 1122 that extends radially inward and is sized to be received within a notch (e.g., the notch 910 of FIGS. 9A-9B) defined in the shaft adapter 400 (FIGS. 4-5 and 9A-9B) or the shaft 202 (FIG. 2). Each arm 1120 may be naturally biased outward and, as described below, a user may provide opposing forces F on the ends of the arms 1120 to seat the tabs 1122 within corresponding notches in preparation for removing the sleeve 422. In some embodiments, as illustrated, a finger grip 1124 may be provided or otherwise defined at the proximal end of each arm 1120, and each finger grip 1124 may provide a location for a user to apply the opposing force F with opposing fingers.

In at least one embodiment, the finger grips 1124 may be angled to provide a mechanical advantage that helps reduce removal force. More specifically, the angle of the finger grips 1124 drives the force vector F toward pushing the sleeve 422 off in the distal direction as opposed to pinching the outer radial surface of the sleeve 422. This may prove advantageous since the sleeve 422 may be secured to the outer radial surface of the shaft adapter 400 via a tight interference fit, and the angled finger grips 1124 may help overcome this engagement.

The blade guard 1108 may be similar in some respects to the blade guard 606 of FIGS. 6A-6B. As best seen in FIG. 11A, the blade guard 1108 provides an elongate, generally cylindrical body 1126 having a closed distal end 1128a and an open proximal end 1128b opposite the distal end 1128a. The body 1126 may be sized and otherwise configured to be received within the sleeve 422, and the distal end 1128a may extend through the aperture 430 of the sleeve 422 when properly installed. Moreover, the distal end 426a of the sleeve 422 may be sized to be received at the ring 1118 of the sleeve extraction tool 1106 when properly installed. Accordingly, the sleeve insertion assembly 1102 forms a nested configuration when properly assembled, where the blade guard 1108 is received within the sleeve 422, the sleeve 422 is partially received within the sleeve extraction tool 1106, and the sleeve extraction tool 1106, the sleeve 422, and the blade guard 1108 are jointly received within the sleeve inserter 1104.

FIGS. 12A and 12B are progressive cross-sectional side views of the sleeve insertion assembly 1102 of FIGS. 11A-11B showing example installation of the sleeve 422, according to one or more embodiments. In FIG. 12A, the sleeve insertion assembly 1102 is assembled with the blade guard 1108 nested within the sleeve 422, the distal end 426a of the sleeve 422 is received within the ring 1118 of the sleeve extraction tool 1106, and the blade guard 1108, the sleeve 422, and the sleeve extraction tool 1106 are all at least partially received within the inner chamber 1114 of the sleeve inserter 1104. In this state, the sleeve insertion assembly 1102 is prepared to deploy the sleeve 422.

In at least one embodiment, the sleeve inserter 1104 may provide or otherwise define a retention mechanism 1202 at the proximal end 1112b. The retention mechanism 1202 may be similar to the retention mechanism 620 of FIG. 6B and, therefore, may be used to help contain the sleeve 422 and the blade guard 1108 within the sleeve inserter 1104 and prevent them from falling out. In some embodiments, as illustrated, the retention mechanism 1202 may comprise a protrusion that extends a short distance into the inner chamber 1114 at the proximal end 1112b, but could alternatively comprise any other structural feature that helps maintain the sleeve 422 and the blade guard 1108 within the sleeve inserter 1104.

In some embodiments, the sleeve insertion assembly 1102 may include a second retention mechanism 1204 at or near the distal end 1112a of the sleeve inserter 1104. The second retention mechanism 1204 may be configured to help retain the blade guard 1108 within the sleeve inserter 1104. In some embodiments, the second retention mechanism 1204 may comprise a tongue-and-groove mated relationship between the blade guard 1108 and the sleeve inserter 1104. In the illustrated embodiment, a protrusion 1206 is defined on the inner radial surface of the inner chamber 1114 of the sleeve inserter 1104, and the protrusion 1206 is sized to be received within a groove 1208 defined on the outer radial surface of the blade guard 1108. Mated engagement between the blade guard 1108 and the sleeve inserter 1104 at the second retention mechanism 1204 may be broken by applying an axial load on the blade guard 1108, as described below.

The blade guard 1108 may define an interior 1210 sized to receive the jaw members 210, 212 of the end effector 204. The blade guard 1108 may be configured to prevent the jaw members 210, 212 from piercing or otherwise engaging the inner wall of the sleeve 422 during installation of the sleeve 422. To accomplish this, the blade guard 1108 may be made of a variety of rigid materials such as, but not limited to, a metal, a thermoplastic (e.g., acrylonitrile butadiene styrene, polycarbonate, polyether ether ketone, etc.), a composite material, and any combination thereof.

To deploy the sleeve 422, the sleeve insertion assembly 1102 is brought into proximity of the end effector 204 and the end effector 204 is first advanced into the inner chamber 1114 of the sleeve inserter 1104. As the end effector 204 enters the inner chamber 1114, the end effector 204 may engage the retention mechanism 1202 at the proximal end 1112b of the sleeve inserter 1104, thus causing the sleeve inserter 1104 to flex outward to receive the end effector 204. The slots 1116 defined in the sleeve inserter 1104 allow the sleeve inserter 1104 to flex open. Moreover, flexing the sleeve inserter 1104 outward disengages the retention mechanism 1202 and thereby allows the sleeve 422 to displace out of the sleeve inserter 1104 during further operation.

The jaw members 210, 212 are aligned with and inserted into the interior 1210 of the blade guard 1108. In some embodiments, the opening of the blade guard 1108 at the proximal end 1128b may be tapered to help receive the jaw members 210, 212 without binding against sharp corners. Inserting the jaw members 210, 212 within the blade guard 1108 prevents the jaw members 210, 212 from inadvertently contacting and potentially cutting the inner wall of the sleeve 422. The user may then advance the sleeve inserter 1104 proximally (i.e., to the right in FIGS. 12A-12B) relative to the end effector 204 and simultaneously advance the sleeve 422 over the end effector 204, the wrist 206, and the shaft adapter 400 (or the shaft 202 of FIG. 2).

The opening of the blade guard 606 at the proximal end 618b is large enough to receive the jaw members 210, 212. Consequently, the entire end effector 204 is prevented from entering the interior 1210. Instead, as the sleeve inserter 1104 is advanced proximally relative to the end effector 204, portions of the end effector 204 will engage the proximal end 1128b of the blade guard 1108 and further proximal movement of the sleeve inserter 1104 will correspondingly urge the blade guard 1108 distally relative to the sleeve 422 and the sleeve inserter 604.

In FIG. 12B, the sleeve inserter 1104 has moved further in the proximal direction relative to the end effector 204. As the sleeve inserter 1104 moves proximally, the blade guard 1108 may be correspondingly urged distally relative to the sleeve 422 as engaged against the end effector 204 at the distal end 1128b of the blade guard 1108. The axial load applied on the blade guard 1108 by the end effector 204 resulting from moving the sleeve inserter 1104 proximally may cause the second retention mechanism 1204 to fail. More specifically, the sleeve inserter 1104 may be made of a flexible material (e.g., silicone), and the axial load placed on the blade guard 1108 by the end effector 204 may cause the protrusion 1206 of the sleeve inserter 1104 to flex out of engagement with the groove 1208 of the blade guard 1108. Once the second retention mechanism 1204 is broken, the blade guard 1108 may be able to move distally generally unobstructed.

In some embodiments, the sleeve inserter 1104 may define or otherwise provide an aperture 1212 at the distal end 1112a, and the distal end 1128a of the blade guard 1108 may extend through the aperture 1212 as the blade guard 1108 moves distally. Since the sleeve inserter 1104 is made of a flexible material, the aperture 1212 may flex and expand radially outward to allow the blade guard 1108 to advance distally.

The sleeve inserter 1104 is advanced proximally relative to the end effector 204 until the sleeve 422 is properly installed over the end effector 204, the wrist 206, and the shaft adapter 400 (or the shaft 202). While the sleeve inserter 1104 is advanced proximally, the arms 1120 of the sleeve extraction tool 1106 are naturally flexed outward and out of engagement with the outer surface of the sleeve 422. In some embodiments, the sleeve inserter 1104 is advanced proximally until the proximal end 426b of the sleeve 422 engages or comes into close contact with the radial shoulder 428 of the shaft adapter 400. In other embodiments, or in addition thereto, the sleeve inserter 1104 may be advanced proximally until the end effector 204 bottoms out, at which point the sleeve 422 will be properly seated against the radial shoulder 428. Once the sleeve 422 is properly installed, the sleeve inserter 1104 may then be retracted distally to thereby remove the sleeve inserter 1104 and the sleeve extraction tool 1106 from the end effector 204 and leave the sleeve 422 installed for use.

The sleeve insertion assembly 1102 may also be used to help remove the sleeve 422 when needed. In such embodiments, the sleeve inserter 1104 and the sleeve extraction tool 1106 may once again be extended over the sleeve 422 and the sleeve inserter 1104 may be advanced proximally and rotated relative to the sleeve 422 until the tabs 1122 of each arm 1120 angularly and axially locate corresponding notches 910 defined at the radial shoulder 428. Once the notches 910 are located, the user may provide a radial inward load F on each arm 1120 at the finger grips 1124, for example, to seat (receive) the tabs 1122 within the notches 910 and thereby place the tabs 1122 at the proximal end 426b of the sleeve 422. The sleeve inserter 1104 and the sleeve extraction tool 1106 may then be retracted distally relative to the shaft adapter 400 and the tabs 1122 may engage the proximal end 426b and simultaneously urge the sleeve 422 in the same direction. Continued distal movement of the sleeve extractor 900 will eventually remove the sleeve 422 from the shaft adapter 400 and the end effector 204.

Embodiments disclosed herein include:

A. A sleeve insertion assembly that includes a sleeve inserter defining an inner chamber and having a distal end and a proximal end opposite the distal end, a sleeve receivable within the inner chamber, and a blade guard receivable within the sleeve and having a cylindrical body that defines an interior and an open end, wherein the open end is sized to receive jaw members of an end effector into the interior but prevent the end effector from entering the interior, and wherein the blade guard is forced out of the sleeve when the sleeve is installed on the end effector.

B. A method of installing a sleeve on an end effector of a surgical tool includes bringing a sleeve insertion assembly into proximity of the end effector, the sleeve insertion assembly having a sleeve inserter, the sleeve positioned within the sleeve inserter, and a blade guard received within the sleeve, inserting jaw members of the end effector into an interior of the blade guard, advancing the sleeve inserter proximally relative to the end effector and thereby advancing the sleeve over the end effector, engaging the sleeve on the blade guard and thereby displacing the blade guard out of the sleeve as the sleeve inserter advances proximally, and preventing the jaw members from contacting the sleeve with the blade guard as the sleeve inserter advances proximally.

C. A sleeve extractor includes a cylindrical body having a distal end and a proximal end, one or more longitudinally-extending fingers defined in the body, and a tab provided on an end of each finger and receivable within a notch defined in a shaft adapter or a shaft of a surgical tool, the notch being located proximal to a proximal end of a sleeve, wherein the sleeve is removed by locating the tab of each finger in a corresponding notch and retracting the body and the sleeve distally relative to the shaft adapter or the shaft.

D. A method of removing a sleeve from an end effector includes extending a sleeve extractor over the sleeve, the sleeve extension device including a cylindrical body having a distal end and a proximal end, and one or more longitudinally-extending fingers defined in the body, axially and angularly aligning the one or more longitudinally-extending fingers with a corresponding one or more notches defined in the shaft adapter or the shaft, applying a radial load on the longitudinally-extending fingers and thereby receiving a tab defined on each finger into the corresponding one or more notches, and moving the sleeve extractor distally relative to the end effector and thereby removing the sleeve from the end effector and the shaft adapter or the shaft.

Each of embodiments A, B, C, and D may have one or more of the following additional elements in any combination: Element 1: wherein the sleeve inserter is made of a material selected from the group consisting of a plastic, a metal, a rubber, an elastomer, silicone, and any combination thereof. Element 2: further comprising a retention mechanism defined at the proximal end of the sleeve inserter to help maintain the sleeve and the blade guard within the sleeve inserter. Element 3: wherein the blade guard is made of a rigid material selected from the group consisting of a metal, a thermoplastic, a composite material, and any combination thereof. Element 4: further comprising one or more longitudinal slots defined in the sleeve inserter and extending from the proximal end toward the distal end. Element 5: further comprising a sleeve extraction tool that provides an annular ring receivable within the inner chamber, one or more arms extending longitudinally from the ring, wherein each arm is received within a corresponding one of the one or more longitudinal slots, and a tab extending from an end of each arm, wherein the tab is receivable within a notch defined in a shaft adapter or a shaft of a surgical tool. Element 6: further comprising a finger grip provided at the end of each arm, wherein the finger grip is angled to provide a mechanical advantage that helps reduce removal force for the sleeve. Element 7: further comprising a retention mechanism at or near the distal end of the sleeve inserter to help retain the blade guard within the sleeve inserter.

Element 8: further comprising displacing the blade guard out of an aperture defined in a distal end of the sleeve inserter as the sleeve inserter advances proximally. Element 9: further comprising extending the sleeve inserter over the sleeve, applying a radial load on the sleeve inserter and thereby gripping an outer radial surface of the sleeve at or near a proximal end of the sleeve, and moving the sleeve inserter and the sleeve distally relative to the end effector and thereby removing the sleeve from the end effector. Element 10: wherein the sleeve inserter defines one or more longitudinally-extending fingers, the method further comprising extending the sleeve inserter over the sleeve, axially and angularly aligning the one or more longitudinally-extending fingers with a corresponding one or more notches defined in a shaft adapter or a shaft of a surgical tool, applying a radial load on the longitudinally-extending fingers and thereby receiving a tab defined on each finger into the corresponding one or more notches, and moving the sleeve inserter and the sleeve distally relative to the end effector and thereby removing the sleeve from the end effector. Element 11: wherein the sleeve inserter defines one or more longitudinal slots extending from the proximal end and the sleeve insertion assembly further includes a sleeve extraction tool providing an annular ring receivable within the sleeve inserter, and one or more arms extending longitudinally from the ring and received within a corresponding one of the one or more longitudinal slots, the method further comprising extending the sleeve inserter and the sleeve extraction tool over the sleeve, axially and angularly aligning the one or more arms with a corresponding one or more notches defined in a shaft adapter or a shaft of a surgical tool, applying a radial load on the one or more arms and thereby receiving a tab defined on each arm into the corresponding one or more notches, and moving the sleeve inserter, the sleeve extraction tool, and the sleeve distally relative to the end effector and thereby removing the sleeve from the end effector and the shaft adapter or the shaft. Element 12: wherein a finger grip is provided on each arm and each finger grip is angled, and wherein applying the radial load on the one or more arms comprises applying the radial load on the finger grip, and reducing a removal force for the sleeve based on an angle of the finger grip relative to the sleeve. Element 13: wherein the sleeve extraction tool has a closed distal end, the method further comprising preventing the jaw members from contacting a user with the sleeve extraction tool and containing the sleeve within the sleeve extraction tool once the sleeve is removed.

Element 14: further comprising a marking provided on the shaft adapter or the shaft to indicate a location of the notch. Element 15: further comprising a cylindrical lock extendable about the body, wherein the cylindrical lock is axially translatable relative to the body to locate the tab of each finger in the corresponding notch. Element 16: wherein the cylindrical lock defines a locking arm having an extension receivable within a slot defined on the body.

By way of non-limiting example, exemplary combinations applicable to A, B, C, and D include: Element 4 with Element 5; Element 5 with Element 6; Element 11 with Element 12; Element 11 with Element 13; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A sleeve insertion assembly, comprising:
   a sleeve inserter defining an inner chamber and having a distal end and a proximal end opposite the distal end;
   a sleeve receivable within the inner chamber; and
   a blade guard receivable within the sleeve and having a cylindrical body that provides an open proximal end, a closed distal end, and an interior extending therebetween,
   wherein the blade guard and the sleeve are jointly received within the inner chamber of the sleeve inserter,
   wherein the open end of the blade guard is sized to receive jaw members of an end effector into the interior but engage portions of the end effector larger than the jaw members and thereby prevent the end effector from fully entering the interior, and
   wherein the blade guard is forced out of the sleeve when the sleeve is installed on the end effector.

2. The sleeve insertion assembly of claim 1, wherein the sleeve inserter is made of a material selected from the group consisting of a plastic, a metal, a rubber, an elastomer, silicone, and any combination thereof.

3. The sleeve insertion assembly of claim 1, further comprising a retention mechanism defined at the proximal end of the sleeve inserter to help maintain the sleeve and the blade guard within the sleeve inserter.

4. The sleeve insertion assembly of claim 3, wherein the retention mechanism comprises a protrusion that extends into the inner chamber.

5. The sleeve insertion assembly of claim 1, wherein the blade guard is made of a rigid material selected from the group consisting of a metal, a thermoplastic, a composite material, and any combination thereof.

6. The sleeve insertion assembly of claim 1, further comprising one or more longitudinal slots defined in the sleeve inserter and extending from the proximal end toward the distal end.

7. The sleeve insertion assembly of claim 6, further comprising a sleeve extraction tool that provides:
   an annular ring receivable within the inner chamber;
   one or more arms extending longitudinally from the ring, wherein each arm is received within a corresponding one of the one or more longitudinal slots; and
   a tab extending from an end of each arm, wherein the tab is receivable within a notch defined in a shaft adapter or a shaft of a surgical tool.

8. The sleeve insertion assembly of claim 7, further comprising a finger grip provided at the end of each arm, wherein the finger grip is angled to provide a mechanical advantage that helps reduce removal force for the sleeve.

9. The sleeve insertion assembly of claim 6, wherein the one or more longitudinal slots comprise two longitudinal slots extending from the proximal end toward the distal end.

10. The sleeve insertion assembly of claim 6, wherein the one or more longitudinal slots exhibit an axial length greater than half a length of the sleeve inserter.

11. The sleeve insertion assembly of claim 1, further comprising a retention mechanism at or near the distal end of the sleeve inserter to help retain the blade guard within the sleeve inserter.

12. The sleeve insertion assembly of claim 1, wherein the closed end of the blade guard extends through a distal aperture of the sleeve when the blade guard is received within the sleeve.

13. A method of installing a sleeve on an end effector of a surgical tool, comprising:
   bringing a sleeve insertion assembly into proximity of the end effector, the sleeve insertion assembly having a sleeve inserter, the sleeve positioned within the sleeve inserter, and a blade guard received within the sleeve such that the blade guard and the sleeve are jointly received within the sleeve inserter;
   inserting jaw members of the end effector into an interior of the blade guard via an open proximal end of the blade guard, the blade guard having a closed distal end opposite the open end;
   advancing the sleeve inserter proximally relative to the end effector and thereby advancing the sleeve over the end effector;
   engaging portions of the end effector larger than the jaw members on the blade guard and thereby displacing the blade guard out of the sleeve as the sleeve inserter advances proximally; and
   preventing the jaw members from contacting the sleeve with the blade guard as the sleeve inserter advances proximally.

14. The method of claim 13, further comprising displacing the blade guard out of an aperture defined in a distal end of the sleeve inserter as the sleeve inserter advances proximally.

15. The method of claim 13, further comprising:
   extending the sleeve inserter over the sleeve;
   applying a radial load on the sleeve inserter and thereby gripping an outer radial surface of the sleeve at or near a proximal end of the sleeve; and
   moving the sleeve inserter and the sleeve distally relative to the end effector and thereby removing the sleeve from the end effector.

16. The method of claim 13, wherein the sleeve inserter defines one or more longitudinally-extending fingers, the method further comprising:
   extending the sleeve inserter over the sleeve;
   axially and angularly aligning the one or more longitudinally-extending fingers with a corresponding one or more notches defined in a shaft adapter or a shaft of the surgical tool;
   applying a radial load on the longitudinally-extending fingers and thereby receiving a tab defined on each finger into the corresponding one or more notches; and
   moving the sleeve inserter and the sleeve distally relative to the end effector and thereby removing the sleeve from the end effector.

17. The method of claim 13, wherein the sleeve inserter defines one or more longitudinal slots extending from a proximal end and the sleeve insertion assembly further includes a sleeve extraction tool providing an annular ring receivable within the sleeve inserter, and one or more arms extending longitudinally from the ring and received within a corresponding one of the one or more longitudinal slots, the method further comprising:
   extending the sleeve inserter and the sleeve extraction tool over the sleeve;
   axially and angularly aligning the one or more arms with a corresponding one or more notches defined in a shaft adapter or a shaft of the surgical tool;
   applying a radial load on the one or more arms and thereby receiving a tab defined on each arm into the corresponding one or more notches; and
   moving the sleeve inserter, the sleeve extraction tool, and the sleeve distally relative to the end effector and thereby removing the sleeve from the end effector and the shaft adapter or the shaft.

18. The method of claim 17, wherein a finger grip is provided on each arm and each finger grip is angled, and wherein applying the radial load on the one or more arms comprises:
   applying the radial load on the finger grip; and
   reducing a removal force for the sleeve based on an angle of the finger grip relative to the sleeve.

19. The method of claim 17, wherein the sleeve extraction tool has a closed distal end, the method further comprising preventing the jaw members from contacting a user with the sleeve extraction tool and containing the sleeve within the sleeve extraction tool once the sleeve is removed.

* * * * *